(12) United States Patent
Voss et al.

(10) Patent No.: US 9,345,475 B2
(45) Date of Patent: May 24, 2016

(54) NEEDLE HARVESTING DEVICES, SYSTEMS AND METHODS

(75) Inventors: Laveille Kao Voss, Belmont, CA (US);
Stephanie Henze, San Mateo, CA (US);
Kristopher M. Konawalik, San Francisco, CA (US); Leah M. Davis, San Francisco, CA (US); Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 904 days.

(21) Appl. No.: 13/610,602

(22) Filed: Sep. 11, 2012

(65) Prior Publication Data
US 2014/0074124 A1    Mar. 13, 2014

(51) Int. Cl.
| | | |
|---|---|---|
| A61B 17/04 | (2006.01) |
| A61M 5/32 | (2006.01) |
| A61B 17/06 | (2006.01) |
| A61B 17/00 | (2006.01) |

(Continued)

(52) U.S. Cl.
CPC ....... *A61B 17/06161* (2013.01); *A61B 17/0057* (2013.01); *A61B 17/0469* (2013.01); *A61B 17/0491* (2013.01); *A61B 17/062* (2013.01); *A61B 17/06061* (2013.01); *A61B 19/0262* (2013.01); *A61B 19/0288* (2013.01); *A61B 2017/00663* (2013.01); *A61B 2017/047* (2013.01); *A61B 2017/0472* (2013.01); *A61B 2017/06142* (2013.01); *A61B 2019/0289* (2013.01); *A61M 5/3278* (2013.01); *A61M 2005/3284* (2013.01)

(58) Field of Classification Search
CPC .................. A61B 17/06161; A61B 17/06061;
A61B 17/0469; A61B 17/0057; A61B 17/062;
A61B 17/0491; A61B 2017/047; A61B
2017/00663; A61B 2017/0472; A61B
2017/06142; A61B 19/0288; A61B 19/0262;
A61B 2019/0289; A61M 5/3278; A61M
2005/3284
See application file for complete search history.

(56) References Cited

U.S. PATENT DOCUMENTS

| | | |
|---|---|---|
| 2,544,282 A | 3/1951 | Sinclair et al. |
| 2,589,499 A | 3/1952 | Lake |
| 2,829,812 A | 4/1958 | Wilson, Jr. |

(Continued)

OTHER PUBLICATIONS

U.S. Appl. No. 13/443,659, filed Apr. 10, 2012, Fortson et al.

(Continued)

*Primary Examiner* — Ryan J Severson
*Assistant Examiner* — Rachel S Papeika
(74) *Attorney, Agent, or Firm* — Workman Nydegger; Randy Shen

(57) ABSTRACT

A needle removal device is provided for removing needles from suturing devices and/or systems. In an embodiment, the needle removal device may be intended for use with a suturing device having one or more needle lumens. The needle removal device may include a first member having a first plurality of needle receptacles extending therethrough. The first needle receptacles may be configured and positioned to correspond to one or more of the one or more needle lumens of the suturing device. The needle removal device may also include a second member having a second plurality of needle receptacles extending therethrough. At least one of the first member or the second member may be moveable between a first position, wherein the first needle receptacles and the second needle receptacles are substantially aligned, and a second position, wherein the first needle receptacles and the second needle receptacles substantially unaligned.

17 Claims, 15 Drawing Sheets

(51) Int. Cl.
*A61B 17/062* (2006.01)
*A61B 19/02* (2006.01)

(56) References Cited

U.S. PATENT DOCUMENTS

| | | | |
|---|---|---|---|
| 4,011,870 A | | 3/1977 | Goldstein |
| 4,373,530 A | | 2/1983 | Kilejian |
| 4,414,908 A | | 11/1983 | Eguchi et al. |
| 4,614,187 A | | 9/1986 | Mulhollan et al. |
| 4,643,341 A | | 2/1987 | Hostetler |
| 4,898,157 A | | 2/1990 | Messroghli et al. |
| 5,002,550 A | | 3/1991 | Li |
| 5,100,421 A | | 3/1992 | Christoudias |
| 5,188,636 A | | 2/1993 | Fedotov |
| 5,415,315 A | * | 5/1995 | Ramirez ............ A61B 19/0288 206/366 |
| 5,417,701 A | | 5/1995 | Holmes |
| 5,458,609 A | | 10/1995 | Gordon et al. |
| 5,476,470 A | | 12/1995 | Fitzgibbons, Jr. |
| 5,480,407 A | | 1/1996 | Wan et al. |
| 5,601,575 A | | 2/1997 | Measamer et al. |
| 5,746,757 A | | 5/1998 | McGuire |
| 5,891,159 A | | 4/1999 | Sherman et al. |
| 6,464,707 B1 | | 10/2002 | Bjerken |
| 6,673,091 B1 | | 1/2004 | Shaffer et al. |
| 6,730,102 B1 | | 5/2004 | Burdulis, Jr. et al. |
| 6,877,352 B1 | | 4/2005 | Schlereth |
| 7,188,756 B1 | | 3/2007 | Storm |
| 7,909,804 B2 | | 3/2011 | Stats |
| 2002/0013603 A1 | | 1/2002 | Green |
| 2003/0029014 A1 | * | 2/2003 | Samuel ............... A61M 5/3205 29/426.4 |
| 2003/0171718 A1 | | 9/2003 | DeLegge et al. |
| 2003/0233119 A1 | | 12/2003 | Tiedemann |
| 2004/0138613 A1 | | 7/2004 | Reid |
| 2004/0158309 A1 | | 8/2004 | Wachter et al. |
| 2005/0038500 A1 | | 2/2005 | Boylan et al. |
| 2005/0125013 A1 | | 6/2005 | Kessler |
| 2007/0016135 A1 | | 1/2007 | Kanner et al. |
| 2007/0135824 A1 | | 6/2007 | O'Brien |
| 2007/0276488 A1 | | 11/2007 | Wachter et al. |
| 2008/0097480 A1 | | 4/2008 | Schorr et al. |
| 2008/0243147 A1 | | 10/2008 | Hamilton et al. |
| 2008/0312740 A1 | | 12/2008 | Wachter et al. |
| 2009/0062743 A1 | | 3/2009 | Rotella et al. |
| 2010/0170812 A1 | * | 7/2010 | Odierno ........... A61B 17/06061 206/63.3 |
| 2011/0106142 A1 | | 5/2011 | Van Furth et al. |
| 2012/0316580 A1 | | 12/2012 | Belman et al. |

OTHER PUBLICATIONS

U.S. Appl. No. 13/610,595, filed Sep. 11, 2012, Voss et al.
U.S. Appl. No. 13/610,598, filed Sep. 11, 2012, Voss et al.
U.S. Appl. No. 13/610,595, Jul. 28, 2014, Office Action.
U.S. Appl. No. 13/610,595, Feb. 4, 2015, Office Action.
U.S. Appl. No. 13/610,595, Oct. 20, 2015, Office Action.
U.S. Appl. No. 13/610,598, Apr. 21, 2015, Office Action.
U.S. Appl. No. 13/610,598, Oct. 21, 2015, Office Action.

* cited by examiner

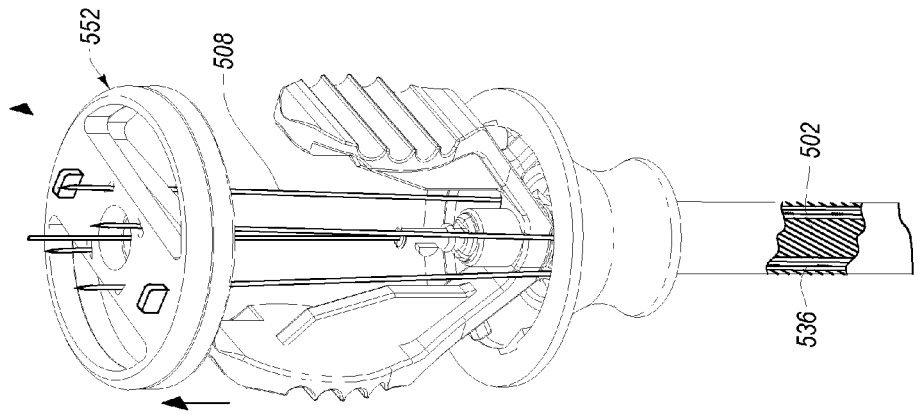
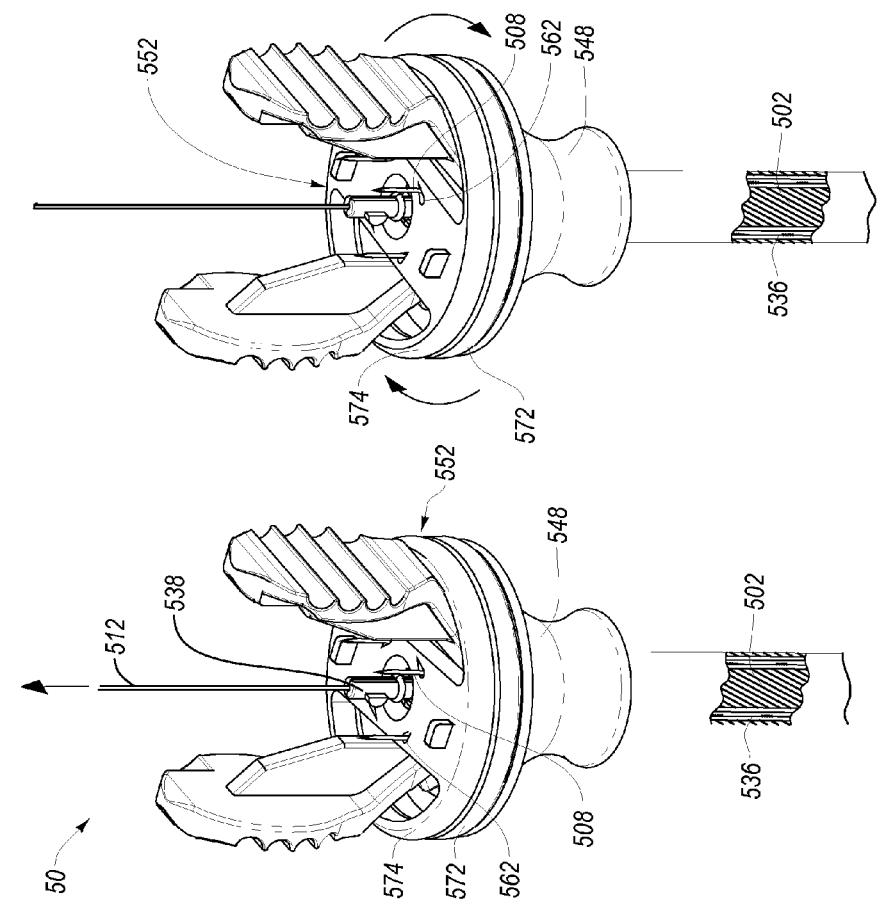

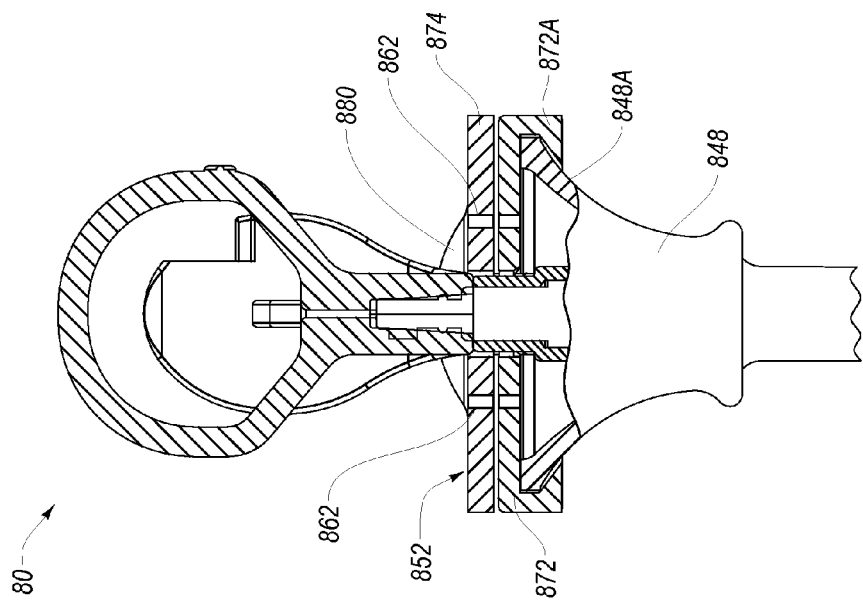
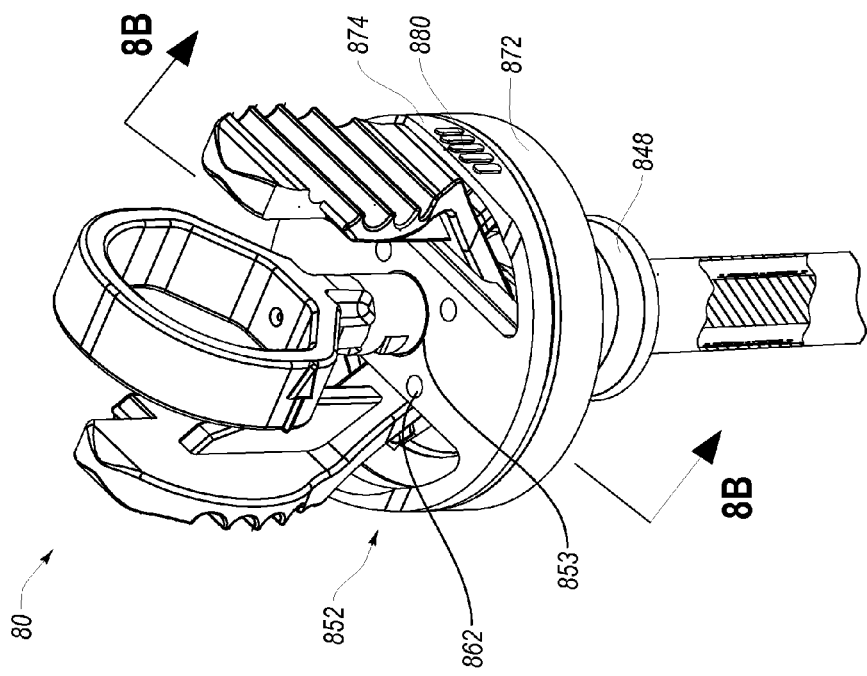
Fig. 8A
Fig. 8B

NEEDLE HARVESTING DEVICES, SYSTEMS AND METHODS

BACKGROUND OF THE INVENTION

1. The Field of the Invention

Embodiments of the invention relate generally to devices, systems, and methods for removing needles from systems or devices used to close openings in body lumens. More particularly, the present invention relates to devices, systems, and methods for removing needles from systems or devices used for closure of arterial and venous puncture sites accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique. Vascular access is generally provided through an introducer sheath, which is positioned to extend from outside the patient's body into the vascular lumen. When vascular access is no longer required, the introducer sheath is removed and bleeding at the puncture site stopped.

One common approach for achieving hemostasis (the cessation of bleeding) is to apply external force near and upstream from the puncture site, typically by manual compression. However, the use of manual compression suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusions and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although trained individuals can reduce the risk of complications, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is another example approach that has been proposed to achieve hemostasis. Generally, the use of bioabsorbable sealing bodies relies on the placement of a thrombogenic and bioabsorbable material, such as collagen, at the superficial arterial wall over the puncture site. While potentially effective, the use of bioabsorbable material suffers from a number of drawbacks. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

A further approach to achieving hemostasis is to use a suture to close a puncture site. Although difficult to suture manually, suture applying devices can be used to appropriately place a suture for closing a puncture site. One example suture applying device has a shaft carrying a pair of needles near its distal end. The needles are joined together by a length of suture. The shaft is used to introduce the needles into a lumen of a body structure and the needles pushed back through the lumen wall on either side of a puncture site. After the needles have passed back through the tissue, they are captured on the shaft and drawn proximally away from the body structure. Drawing the needles outward leaves a loop of suture behind to close the puncture site. The loop of suture can then be tied in a knot to complete the closure. Suture applying devices address many disadvantages associated with the use of external force (e.g., digital compression) and with the use of bioabsorbable sealable bodies to achieve hemostasis.

However, the use of suture applying devices also has a number of inefficiencies. Typically, to access a suture in manner that it can be tied off, the needle must be fully removed from the shaft and other components subsequently moved out of the way. However, after needle deployment, suture applying devices are often configured to draw needles proximally only to a point where they are partially exposed at the proximal end of the shaft. To remove needles from the shaft completely, an operator has to use manual force to individually grab the proximal end of each needle (e.g., with a hemostat) and draw it further proximally while also securely holding the shaft. The amount of force required to further draw the needle proximally can sometimes be quite large (and potentially unacceptable).

Some suture applying devices have a separate internal needle holder that can be used to receive a partially exposed needle. The needle holder assists an operator in drawing the needle proximally until the distal end of the needle exits the proximal end of the shaft. However, needle holders often do not sufficiently grip a needle such that it can be efficiently drawn proximally. Additionally, the leverage obtained from using a needle holder is often insufficient to remove a needle from challenging (e.g., calcified or scarred) tissue anatomy.

For at least these reasons, it would be desirable to provide devices and methods for more efficiently removing needles from a suture applying device. It would be particularly desirable to provide devices and methods for efficiently removing needles from a suture applying device used to suture a puncture site associated with a percutaneous vascular procedure.

BRIEF SUMMARY OF THE INVENTION

Embodiments of the invention relate generally to devices, systems, and methods for removing needles from systems or devices used to close openings in body lumens. In an embodiment, the needle removal device may be intended for use with a suturing device having one or more needle lumens. The needle removal device may include a first member having a first plurality of needle receptacles extending therethrough. The first needle receptacles may be configured and positioned to correspond to one or more of the one or more needle lumens of the suturing device. The needle removal device may also include a second member having a second plurality of needle receptacles extending therethrough. At least one of the first member or the second member may be moveable between a first position, wherein the first needle receptacles and the second needle receptacles are substantially aligned, and a second position, wherein the first needle receptacles and the second needle receptacles substantially unaligned.

In an embodiment, the first position may be configured to allow one or more needles to be moveable within at least one of the first needle receptacles or the second needle receptacles and the second position may be configured to at least partially deform the one or more needles between the first member and the second member to substantially lock the one or more needles within at least one of the first needle receptacles or the second needle receptacles.

In an embodiment, a suture system may include a plurality of needles. One or more sutures may have an end attached to one of the needles. The system may also include a guide body having a proximal end, a distal end, an internal lumen configured to receive at least a portion of the one or more sutures, and a plurality of needle lumens configured to receive the needles. A shaft may be moveably positioned within the central lumen of the guide body. The shaft may be operably connected to the needles such that proximal movement of the shaft draws the needles into the needle lumens. The system may also include a needle removal device removably attached to the proximal end of the guide body. The needle removal device may include a first member having a first plurality of needle receptacles extending therethrough. The first needle receptacles may be configured and positioned to correspond to one or more of the needle lumens of a suturing device. The needle removal device may also include a second member having a second plurality of needle receptacles extending therethrough. At least one of the first member or the second member may be moveable between a first position, wherein the first needle receptacles and the second needle receptacles are substantially aligned, and a second position, wherein the first needle receptacles and the second needle receptacles are substantially unaligned.

In an embodiment, a method for removing one or more needles from a suturing device having one or more needle lumens may include positioning a needle removal device adjacent a proximal end of the suturing device. The needle removal device may include a first member having a first plurality of needle receptacles extending therethrough. The first needle receptacles may be configured and positioned to correspond to one or more of the one or more of the needle lumens of the suturing device. The needle removal device may also include a second member having a second plurality of needle receptacles extending therethrough. At least one of the first member or the second member may be moveable between a first position, wherein the first needle receptacles and the second needle receptacles are substantially aligned, and a second position, wherein the first needle receptacles and the second needle receptacles are substantially unaligned. The method may also include drawing the needles proximally through the suturing device until at least tips of the needles exit from the proximal end of the suturing device. The method may include receiving at least the tips of the needles within one or more of the first needle receptacles and one or more of the second needle receptacles. The method may further include moving at least one of the first member or the second member to the second position to at least partially deform at least a portion of the needles between the first member and the second member. Finally, the method may include moving the needle removal device proximally relative to the suturing device to remove the needles from the suturing device.

These and other advantages and features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 6A-6C illustrate steps for removing needles from the suturing system shown in FIG. 5A;

FIG. 8A illustrates a perspective view of a needle removal device according to another embodiment; and FIG. 8B illustrates a cross-sectional view of the needle removal device shown in FIG. 8A taken along section line 8B-8B.

DETAILED DESCRIPTION OF THE PREFERRED EMBODIMENTS

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

The term "suturing" is herein intended to include the process of joining two surfaces or edges together with a suture such as a thread of material (either polymeric or natural), gut, wire, or the like or so as to close an aperture, opening, or wound, or join tissues.

Figure 1A:
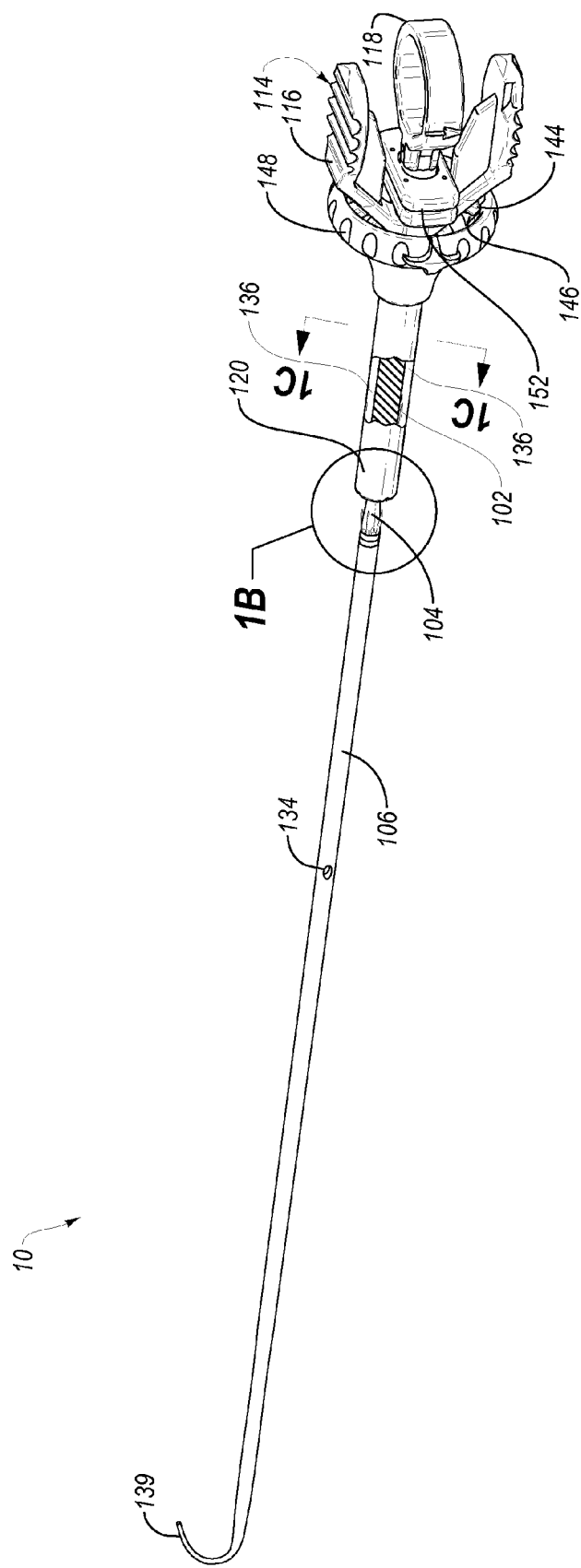
FIG. 1A illustrates a perspective view of a suturing system according to an embodiment.
Figure 1B:
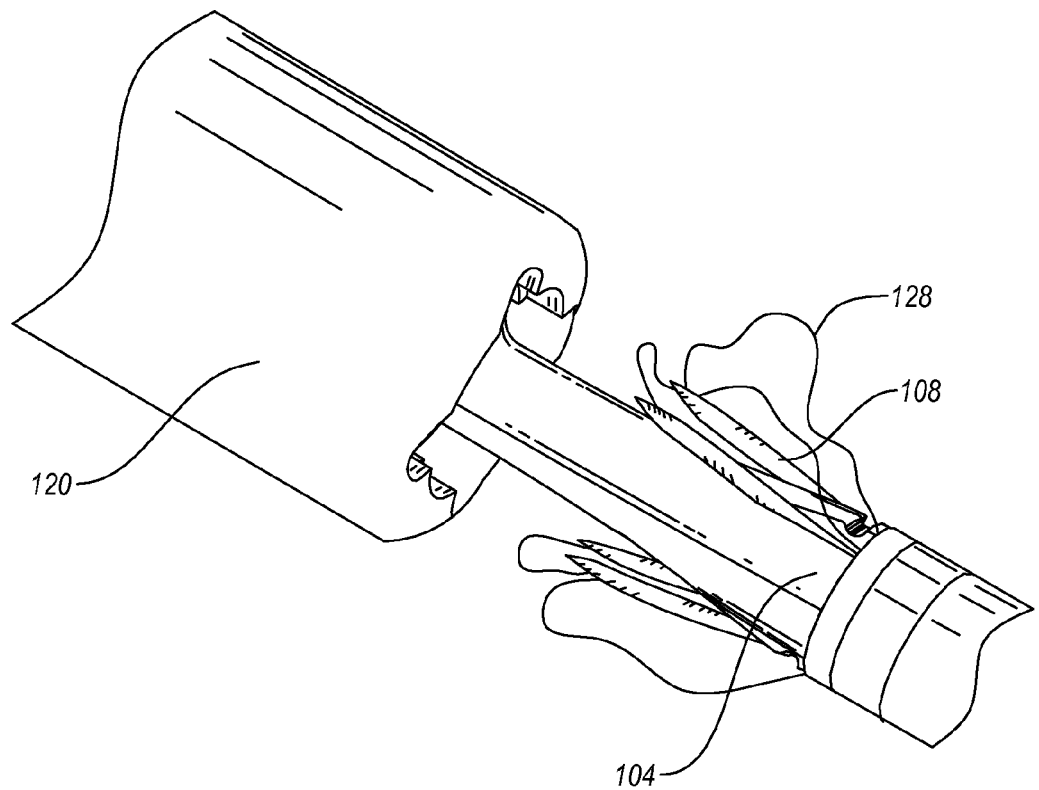
FIG. 1B illustrates a detailed view of the needle guide of the suturing device of FIG. 1A taken along line 1B-1B.

Referring to FIG. 1A and FIG. 1B, a suturing system 10 may be provided to close openings in body tissues. The suturing system 10 may comprise a guide body 102, a needle guide 104 secured to a distal end of the guide body 102, and a flexible tube 106 secured to a distal end of the needle guide 104. A plurality of needles 108 may be mounted with their distal ends in a support holster (not shown) within the flexible tube 106. In an embodiment, a moveable needle deployment shaft 112 (shown in FIG. 1C) may be operatively connected to the needles 108. For example, the needle deployment shaft 112 may be attached to the support holster and may be moveably positioned within a central lumen 122 (shown in FIG. 1C) that extends at least partially through the flexible tube 106, the needle guide 104, and the guide body 102. As shown further in regard to FIGS. 2A-2D, the guide body 102 of the suturing system 10 may be introduced within a percutaneous tissue tract leading to a puncture site with the flexible tube 106 positioned within a vessel. When the needle deployment shaft 112 is moved proximally relative to the guide body 102, the needles 108 may be drawn proximally through the flexible tube 106, out the needle guide 104 and toward the guide body 102. The needles 108 may carry suture lengths 128 (shown in FIG. 1B) which may be used to close the puncture site. As the needles 108 extend from the needle guide 104, the needles 108 may pass through tissue positioned between the needle guide 104 and the guide body 102. The guide body 102 may then capture the needles 108 and route them toward the user.

A handle assembly 114 may be attached to a proximal end of the guide body 102. The handle assembly 114 may include interlock wings 116, a needle removal device 152, and a handle 118. In an embodiment, the handle 118 may be attached to a proximal end of the needle deployment shaft 112 and can be pulled proximally in order to actuate the needle deployment shaft 112. A sheath 120 may also be rotatably received over the guide body 102. The sheath 120 may be sized to be introducible through the percutaneous tissue tract. The sheath 120 may be inflexible or flexible and formed at least partially from metal, a hard plastic or polymer material, or other suitable materials.

Figure 1C:
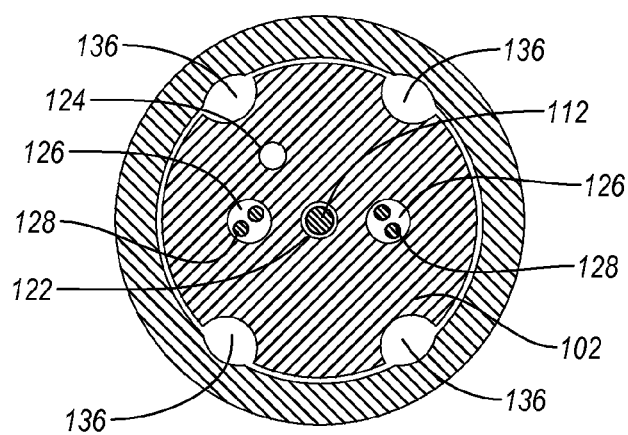
FIG. 1C illustrates a cross-sectional view of the suturing system of FIG. 1A taken along line 1C-1C.

As best shown in FIG. 1C, the guide body 102 may define one or more axial lumens or channels therein. For example, the central axial lumen 122 may be provided for slidably receiving the needle deployment shaft 112. The guide body 102 may also include one or more blood detection lumens 124 and one or more suture lumens 126 that pass therethrough. The one or more blood detection lumens 124 may be configured for receiving blood from the vessel to assist in positioning the suturing system 10. The one or more suture lumens 126 may be configured to receive the suture lengths 128 attached to the needles 108. In other embodiments, the blood detection lumen 124 may be omitted.

The guide body 102 may further include a plurality of needle lumens 136. In an embodiment, the needle lumens 136 may be axially aligned and circumferentially spaced about the periphery of the guide body 102. In other embodiments, the needle lumens 136 may be configured to extend through the guide body 102. In yet other embodiments, the needle lumens 136 may be configured to extend along paths wherein the needle lumens 136 exit along a single side of the guide body 102 as described, for example, in U.S. patent application entitled "Removing Needles from a Suturing Device," Ser. No. 13/610,595, filed on the same day, the disclosure of which is incorporated herein in its entirety. The needles 108 may enter the distal ends of the needle lumens 136 after the needles 108 exit the needle guide 104.

Referring again to FIG. 1A, the flexible tube 106 may be formed from a flexible plastic, polymer, metal, combinations thereof, or any other suitable material. The flexible tube 106 may be generally circular in cross-sectional geometry and may include a guide wire lumen (not shown) and the central lumen (not shown) configured to house the support holster (not shown) and the needles 108. The flexible tube 106 may further include a guide wire exit port 134 configured to allow a guide wire that is advanced proximally through a guide wire lumen (not shown) to exit from a side of the flexible tube 106. Optionally, the flexible tube 106 may include a distal J-tip 139 for atraumatic tracking through vessels or other body lumens. In other embodiments, the distal J-tip 139 may be omitted.

Construction of the handle assembly 114 will now be described. A stem 138 (shown in FIG. 2B) may be formed between the interlock wings 116 for receiving the handle 118. The stem 138 may include a key 130 that is received into a slot (not shown) in the handle 118. Such a configuration may allow the handle 118 to be slid into the stem 138 with the key being received into the slot. The handle 118 may be rotated in a clockwise direction to secure the handle 118 to the stem and prevent axial translation of the needle deployment shaft 112. To move the needle deployment shaft 112 and deploy the needles 108, the handle 118 may be rotated in a counter-clockwise direction so that the key may be pulled from the slot. The handle 118 may then be proximally moved to deploy the needles 108.

In an embodiment, the handle assembly 114 may be securely attached to the guide body 102 so that the sheath 120 may be rotated relative to the guide body 102 when holding the handle assembly 114. The handle assembly 114 may be securely fastened to the guide body 102 by gluing, molding, and the like. In other embodiments, the handle assembly 114 may be formed as an integral part of the guide body 102. The handle assembly 114 may also include a plurality of tubes (not shown) aligned with the blood detection lumen 124 and the one or more suture lumens 126. At least a portion of the suture lengths may pass through one or more of the tubes.

In an embodiment, the interlock wings 116 may each include a detent 144 for engaging a pair of grooves 146 in a hub 148 of the sheath 120. The interlock wings 116 may be constructed of a resilient material (e.g., polycarbonate) so that the interlock wings 116 may be pressed together to remove the detents 144 from the grooves 146. Upon removal of the detents 144 from the grooves 146, the sheath 120 may be rotated relative to the guide body 102 by maintaining a grip on the interlock wings 116 with one hand and rotating the hub 148 with the other hand. In other embodiments, the interlock wings 116 and the hub 148 may allow a physician or other user to hold and manipulate the suturing system 10. For example, the physician can hold on to the hub 148 when inserting and withdrawing the suturing system 10 from a puncture site.

Referring now to FIGS. 1A and 1C, the central lumen 122 may extend from the flexible tube 106, through the needle guide 104, through the guide body 102 and into the stem 138 of the handle assembly 114. The needle deployment shaft 112 may run the length of the central lumen 122. Accordingly, the handle 118 may be proximally moved to move the needle deployment shaft 112 through the central lumen 122 which in turn moves the needles 108. The one or more suture lumens 126 may run generally parallel or non-parallel to the central lumen 122. The suture lengths 128 may pass through the one or more suture lumens 126. In one embodiment, the suture lengths 128 may be configured in the form of the loop with the free ends being attached to the needles 108 and with the looped end passing outside the suturing system 10 through the tube (not shown). Such a configuration facilitates management of the suture lengths 128 during insertion of the suturing system 10 to a puncture site and during movement of the needles 108 to suture the vessel wall. As the needles 108 are proximally advanced through the guide body 102, the suture lengths 128 are drawn distally through the suture lumen 126 where they are completely removed from the suture lumen 126 upon full deployment of the needles 108 wherein the tips of the needles 108 exit the hub 148 and are received by the needle removal device 152 positioned at the proximal end of the guide body 102. The needle removal device 152 may be configured to selectively grasp or pinch the needles 108 exiting from the hub 148 and to draw the needles 108 proximally out of the guide body 102 until the suture lengths 128 are available to a user to be tied over the puncture site.

As shown in FIG. 1A, the needle removal device 152 may be positioned at least partially within the hub 148. In other embodiments, the needle removal device 152 may be selectively positioned distally or proximally of the hub 148.

Figure 1D:
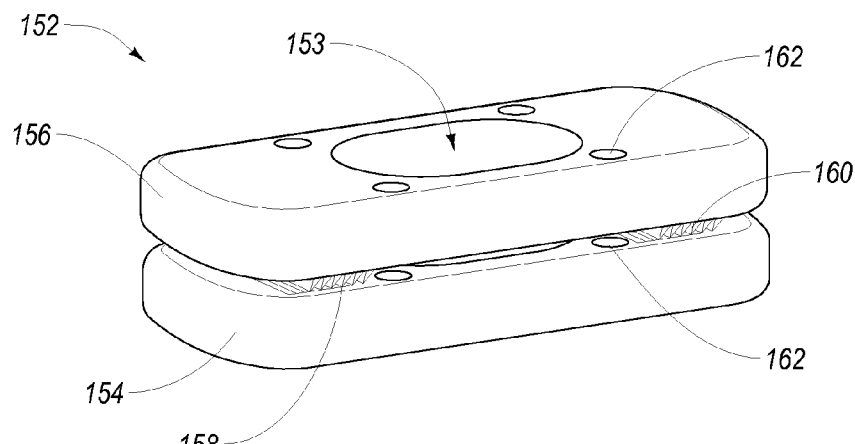
FIG. 1D illustrates a perspective view of the needle removal device removed from the suturing system shown in FIG. 1A according to an embodiment.
Figure 1E:
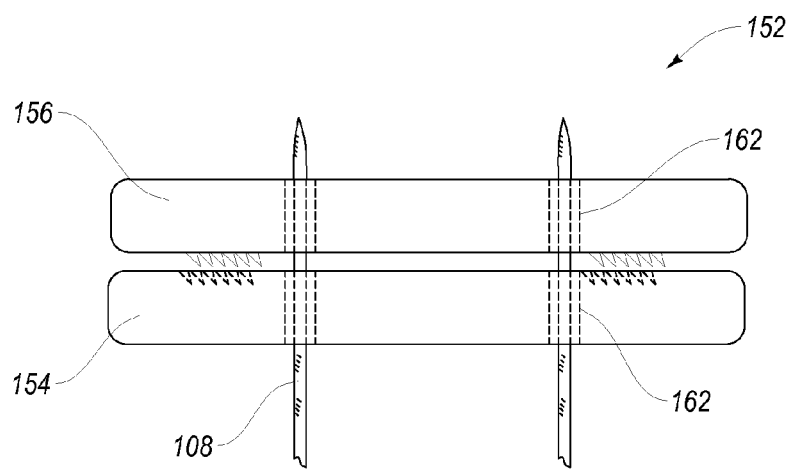
FIGS. 1E and 1F illustrate side views of the needle removal device shown in FIG. 1D in various configurations.
Figure 1F:
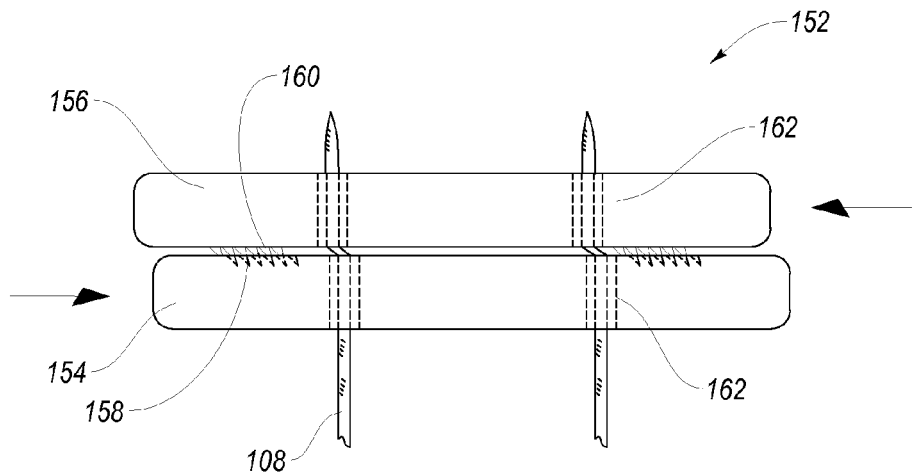

FIGS. 1D-1F show the needle removal device 152 removed from the suturing system 10. In an embodiment, the needle removal device 152 may include a first member 154 and a second member 156 slidably attached to one another. As shown, the first member 154 and the second member 156 may have a generally rounded rectangular shape. In other embodiments, the first member 154 and/or the second member 156 may have a generally cylindrical shape, a generally oval shape, or any other suitable shape. The first member 154 and/or the second member 156 may be made from polymers, polymeric composites, titanium, stainless steel, metal alloys, combinations thereof, or any other suitable materials. As shown, a central aperture 153 may extend through the first member 154 and the second member 156 and may be configured to allow the stem 138 of the handle assembly 114 to pass through the needle removal device 152 such that the needle removal device 152 may be selectively positioned between the guide body 102 and the handle 118. The central aperture 153 may also be configured to receive the needle shaft 112 such that the needle shaft 112 may selectively be drawn through the needle removal device 152. For example, the central aperture 153 may have a generally rounded rectangular shape, a generally rectangular shape, a generally oval shape, a generally circular shape, a generally square shape, combinations thereof, or any other suitable shape. Such a configuration allows the needle shaft 112 and the needle removal device 152 to move axially relative to one another.

The first member 154 and the second member 156 may include a plurality of needle receptacles 162 extending therethrough. One or more of the needle receptacles 162 may have a generally cylindrical shape, generally conical shape, generally oval shape, a generally teardrop-like shape, or any other suitable geometric shape. The needle receptacles 162 may be configured and positioned in the first member 154 and/or the second member 156 to generally correspond to the needle lumens 136 exiting the proximal end of the guide body 102. Such a configuration allows the needles 108 to be selectively received within the needle receptacles 162 when the needles 108 exit the needle lumens 136 of the guide body 102. While four needle receptacles 162 in both the first member 154 and the second member 156 are shown surrounding the central aperture 153, three, five, six, or any other suitable number of needle receptacles 162 may be possible in any suitable configuration.

The needle removal device 152 may be configured to selectively secure the needles 108 within the needle removal device 152. For example, the needle removal device 152 may be moveable between a first position or receiving position as shown in FIG. 1E, wherein the needle receptacles 162 of the first member 154 and the second member 156 are substantially aligned, and a second position or deforming position, wherein the needle receptacles 162 of the first member and the needle receptacles 162 of the second member 156 are substantially unaligned as shown in FIG. 1F. The first member 154 may move relative to the second member 156, the second member 156 may move relative to the first member 154, or the first member 154 and the second member 156 may both move relative to one another. In the receiving position, the needle receptacles 162 of the first member 154 and the needle receptacles 162 of the second member 156 may be substantially aligned relative to one another and at least a portion of each needle 108 may freely pass through the needle receptacles 162. In the deforming position, the first member 154 and/or the second member 156 may slide relative to one another which in turn may move the needle receptacles 162 of the first member 154 and the needle receptacles 162 of the second member 156 substantially out of alignment. The relative movement of the first member 154 and/or the second member 156 may exert one or more shear forces on the portion of the needles 108 extending through the needle receptacles 162 to at least partially deform the needles 108 such that the needle 108 become pinched or stuck between the first member 154 and the second member 156. Thus, the needle removal device 152 provides a relatively strong grip or hold on the needles 108. In the deforming position, the needle removal device 152 may also be configured to allow a user to remove the needles 108 from the suturing system 10. A user may use the needle removal device 152 in order to exert a force in the proximal direction on the needles 108 to overcome an initial resistance to removal of the needles 108 from the guide body 102. For example, the needle removal device 152 may allow a user to exert a force of about one quarter (0.25) pound-force to seventy (70) pound-force; about one (1) pound-force to sixty (60) pound-force; or about five (5) pound-force to forty (40) pound-force on the needles 108. In other embodiments, the needle removal device 152 may allow the user to exert larger or smaller forces on the needles 108.

The needle removal device 152 may include locking features configured to selectively lock the needle removal device 152 in the deforming position. For example, the first member 154 may include a plurality of teeth 158 formed in a top surface of the first member 154. The second member 156 may include a plurality of teeth 160 of complimentary shape, configured to interlock with one or more of the teeth 158 of the first member 154 when the needle removal device 152 is in the deforming position. Such a configuration may allow a user to conveniently and beneficially lock the needle removal device 152 in the deforming position before removing the needles 108 from the guide body 102. In other embodiments, the locking feature may include a detent formed in the first member 154 and a groove formed in the second member 156 configured to engage the detent when the needle removal device 152 is in the deforming position. In other embodiments, the locking features may be omitted.

FIGS. 2A-2D illustrate steps for removing the needles 108 from the suturing device 10 with the needle removal device 152. While the method is illustrated using the suturing system 10 and the needle removal device 152, it will be appreciated that the described method may utilize any other suturing system or needle removal device disclosed herein. Moreover, for ease of reference, one of the interlock wings 116 has been removed from the suturing system 10.

Figure 2A:
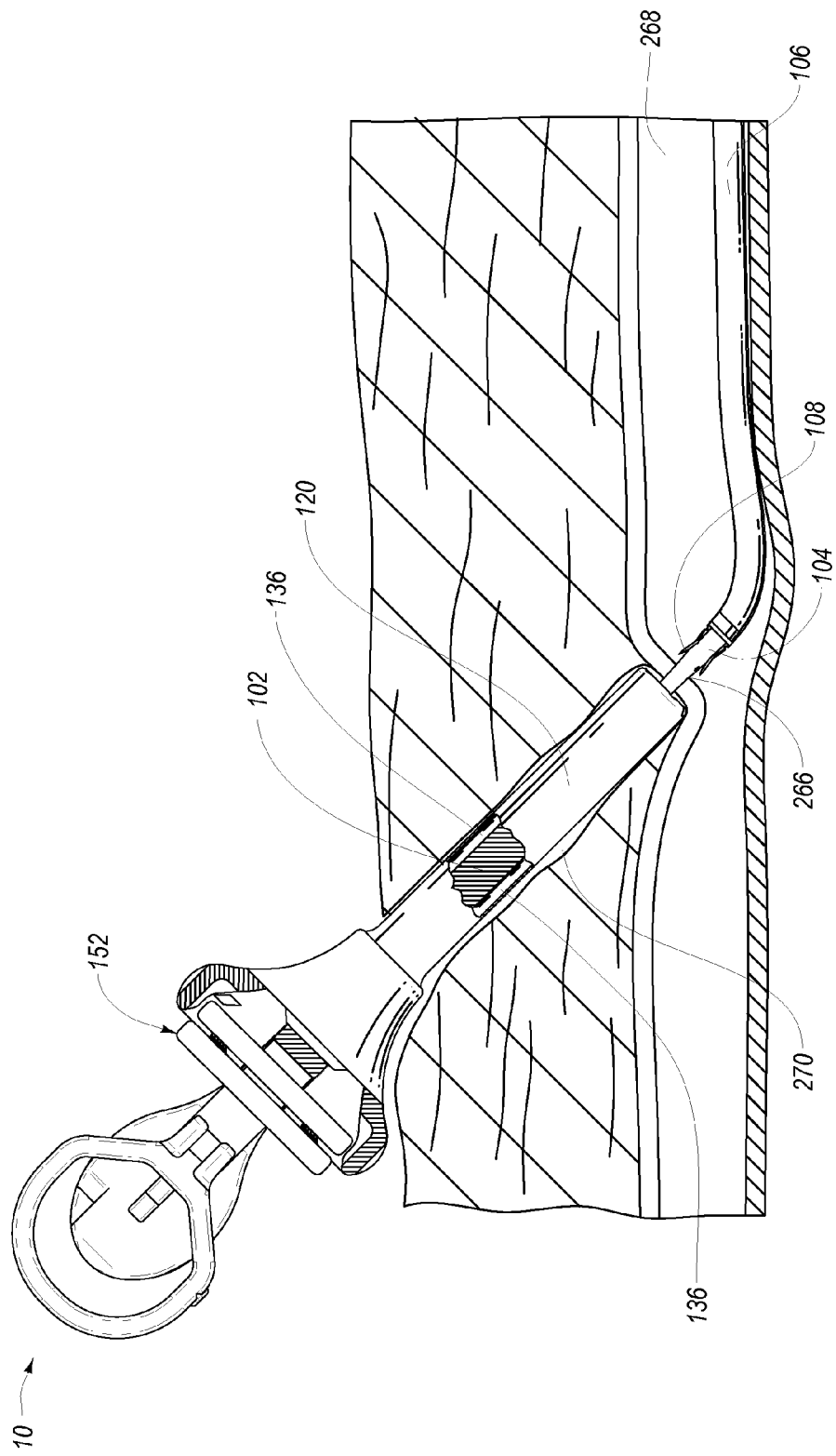
FIGS. 2A-2D illustrate steps for removing needles from the suturing device shown in FIG. 1A.

Referring now to FIG. 2A, the method can begin by advancing the suturing system 10 through an access tract 270 to position the needles 108 encased by the flexible tube 106 within the vessel 268 past the puncture site 266. In other embodiments, the suturing system 10 may be introduced over a guide wire (not shown) passing through the vessel 268. For example, an introducer sheath (not shown) may be placed over a guide wire passing percutaneously beneath the patient's skin. The introducer sheath may then be withdrawn from the puncture site 266 by sliding the introducer sheath over the guide wire. The suturing system 10 may then be introduced over the guide wire by passing the guide wire proximally through the flexible tube 106 until the guide wire exits the exit port 134 (shown in FIG. 1A). The flexible tube 106 may then be further advanced over the guide wire until the needle guide 104 is about to enter the access tract 270. At this point, the guide wire may be pulled from the flexible tube 106 and is withdrawn from the puncture site 266. With the guide wire removed, the suturing system 10 may be further advanced into the vessel 268 to pass the needle guide 104 through the access tract 270 into the vessel 268.

Figure 2B:
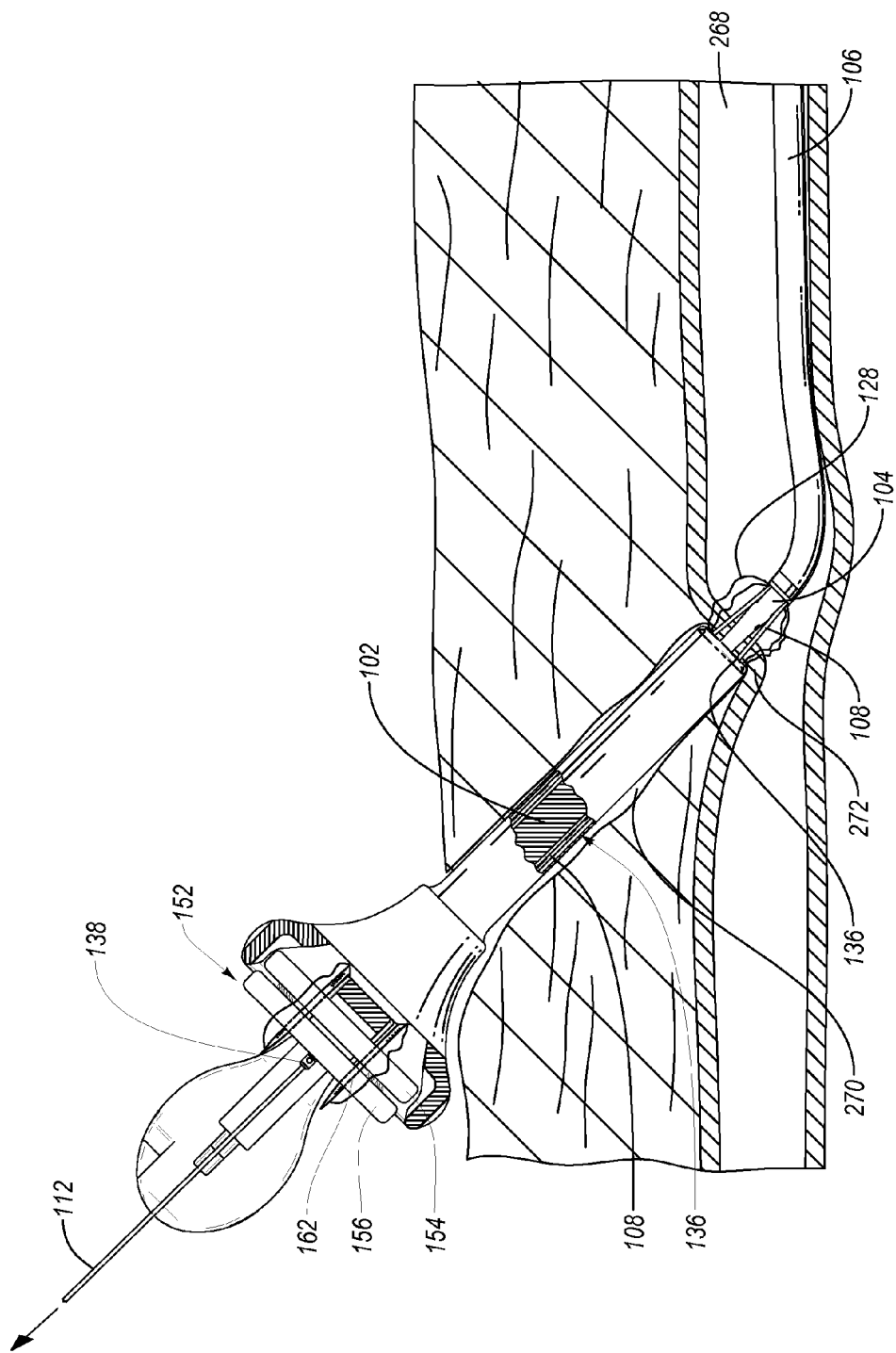

Referring now to FIG. 2B, to deploy the needles 108, the handle 118 (shown in FIG. 2A) may be drawn proximally relative to the guide body 102 to proximally move the needle shaft 112. In other embodiments, the handle 118 may be rotated counter-clockwise to disengage the key from the slot in the stem 138 prior to drawing the handle 118 proximally. As shown, the needles 108 will exit from the needle guide 104, pass through the vessel wall 272, and will be directed toward the needle lumens 136 of the guide body 102. As the needles 108 are drawn through the vessel wall 272, the suture lengths 128 will be fed through the one or more suture lumens 126 (shown in FIG. 1C). The needles 108 will then be advanced into the needle lumens 136, with the suture lengths 128 being continually fed through the one or more suture lumens 126. The handle 118 may continue to be drawn proximally (i.e., outward from the patent) in order to continue to pull the needles 108 through the guide body 102. Such movement of the needles 108, in turn, continues to draw the needles 108 proximally through the needle lumens 136 of the guide body 102 until the needles 108, with the suture lengths 128 still attached thereto, exit the hub 148 and are received within the needle receptacles 162 of the needle removal device 152 as shown in FIG. 2B. At that point, the looped portions of the suture lengths 128 may be removed from the one or more suture lumens 126.

Figure 2C:
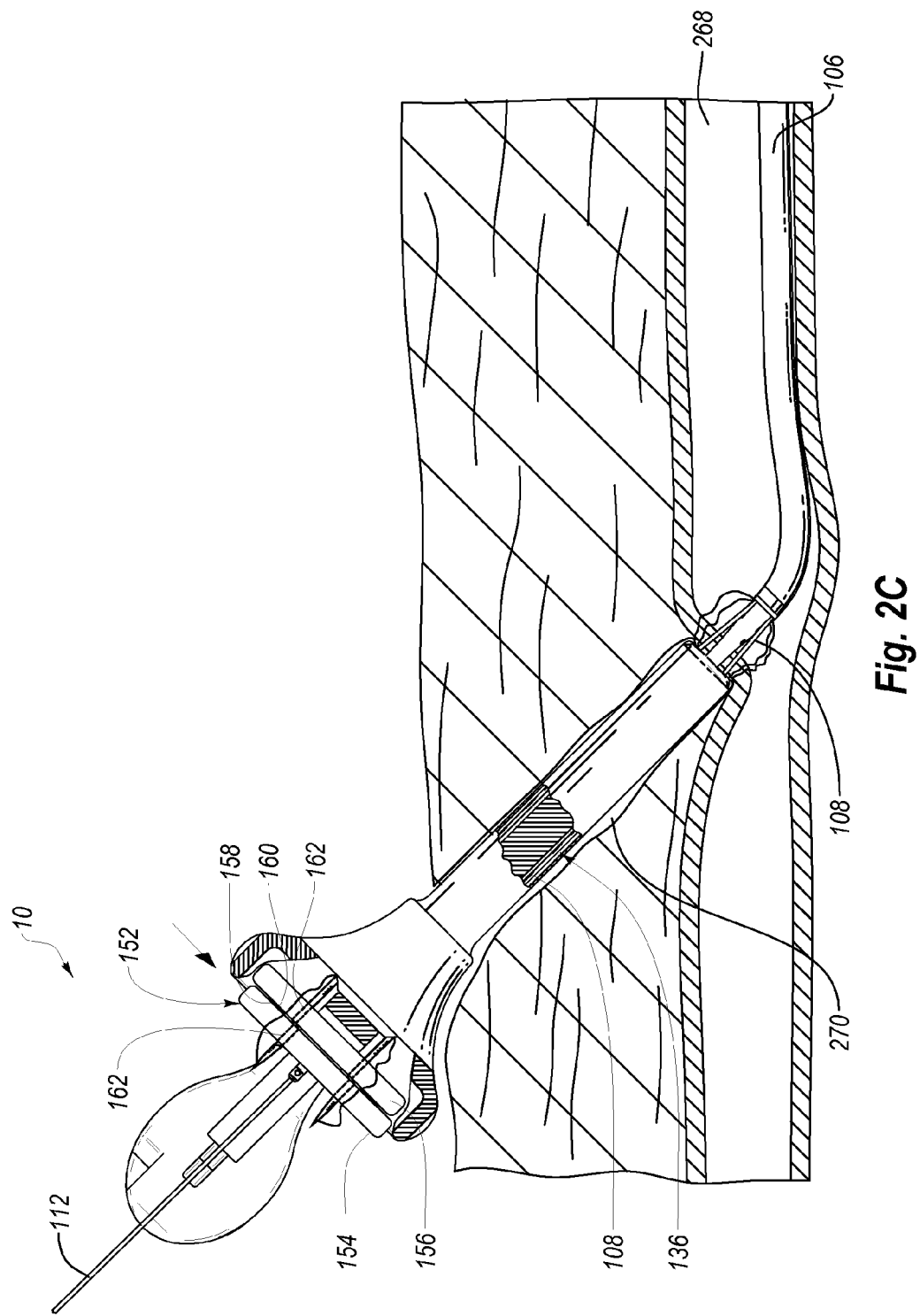

Referring now to FIG. 2C, the first member 154 and/or the second member 156 may be squeezed or pushed toward the needles 108 such that the needle removal device 152 moves toward the deforming position. As the needle removal device 152 moves to the deforming position, the first member 154 and/or the second member 156 may at least partially deform the portions of the needles 108 extending through the needle receptacles 162 such that the needles 108 become pinched or locked between the first member 154 and the second member 156. In the deforming position, one or more of the teeth 158 of the first member 154 may interlock with one or more of the teeth 160 of the second member 156 to lock or secure the needle removal device 152 in the deforming position.

Figure 2D:
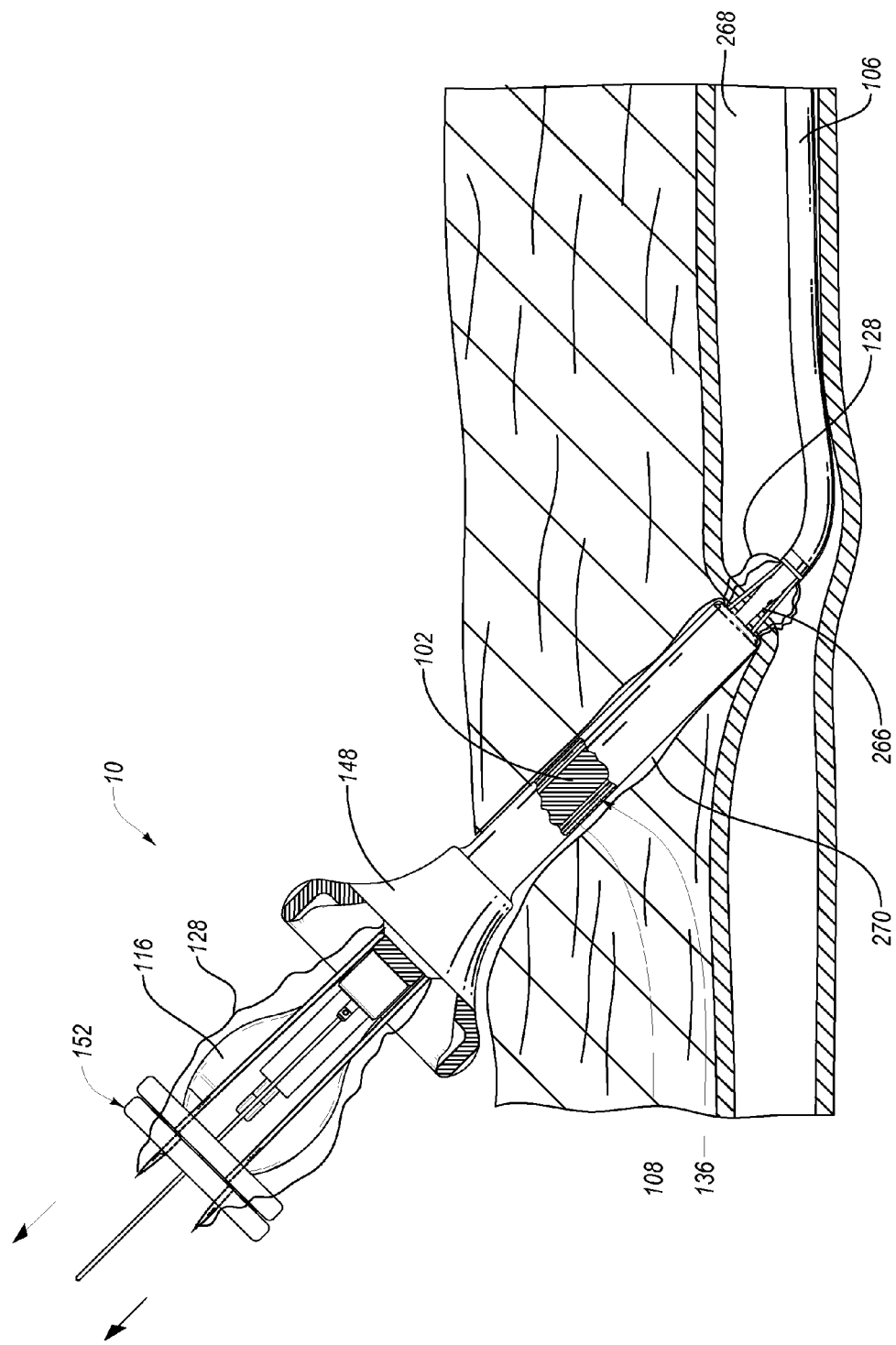

Referring now to FIG. 2D, with the needle removal device 152 locked in the deforming position, the needle removal device 152 may be moved proximally relative to the guide body 102. Proximal movement of the needle removal device 152, in turn, may continue to remove the needles 108 from the guide body 102 until the suture lengths 128 are available to the user. Once the needles 108 are removed from the guide body 102, slack may be removed from the suture lengths 128 by pulling them to evenly matched lengths and tensioning until resistance is felt. The suture lengths 128 may then be cut substantially close to the needles 108 and the needles 108 may be disposed of. The suturing system 10 may then be removed from the access tract 270 to allow closure of the puncture site 266. Such a configuration of the suturing system 10 may allow a user to safely and securely close a puncture site.

In other embodiments, the suturing system 10 may be readily adapted for use with punctures made to a variety of hollow body organs and lumens. It may, however, be necessary to modify the dimensions and other particular aspects of the suturing system 10 to accommodate the different usage environments. For example, the distance separating the needle guide 104 and the distal end of the guide body 102 may be configured to allow transapical insertion of the suturing system 10 into a heart ventricle as described in U.S. patent application, entitled "Apparatus and Method for Suturing Body Lumens," Ser. No. 13/443,659, the disclosure of which is incorporated herein in its entirety.

Another embodiment of a needle removal device will now be described in relation to FIGS. 3A through 4C. A suturing system 30 may be similar in many respects to the suturing system 10 previously described above in FIGS. 1A-2D. To the extent features or components of this configuration function in a manner similar to that as described above, such disclosure is hereby incorporated into the following additional configuration. Like structures and/or components are given like reference numerals. For ease of reference, only the proximal portion of the suturing system 30 is shown and described. The distal components may be manipulated by the proximal components in a similar manner as described with references to FIGS. 1A through 2D.

Figure 3A:
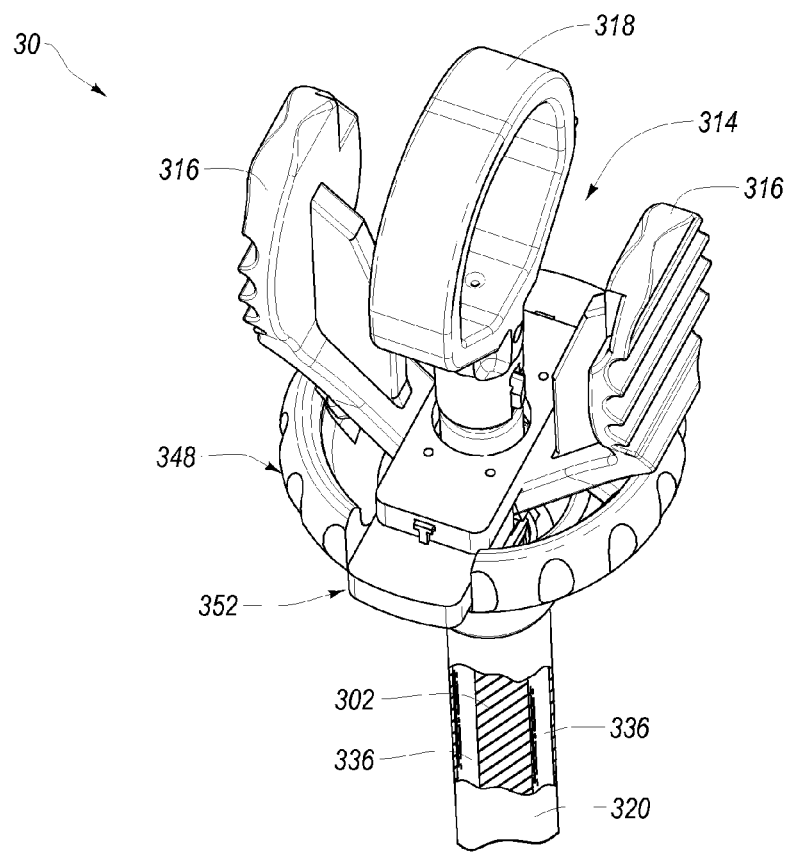
FIG. 3A illustrates a partial perspective view of a suturing system according to another embodiment.

FIG. 3A is a partial perspective view of the suturing system 30. The suturing system 30 may include a guide body 302, a needle guide (not shown) secured to a distal end of the guide body 302, and a flexible tube (not shown) secured to a distal end of the needle guide. A sheath 320 may be received over the guide body 302. A plurality of needles 308 (shown in FIG. 3C) may be mounted with their distal ends in a support holster (not shown) and attached to a movable needle deployment shaft 312 (shown in FIG. 4A). A handle assembly 314 may be attached to a proximal end of the guide body 302. The handle assembly 314 may include a pair of interlock wings 316, a needle removal device 352, and a handle 318. The handle 318 may be attached to a proximal end of the needle shaft 312 and may be pulled proximally in order to draw needles 308 (shown in FIG. 4A) from the flexible tube (not shown), through the needle guide (not shown) and into the guide body 302 until the tips of the needles 308 emerge from the guide body 302 within a hub 348 of the sheath 320. Once the needles 308 emerge within the hub 348, the needles 308 may be received within the needle removal device 352.

Figure 3B:
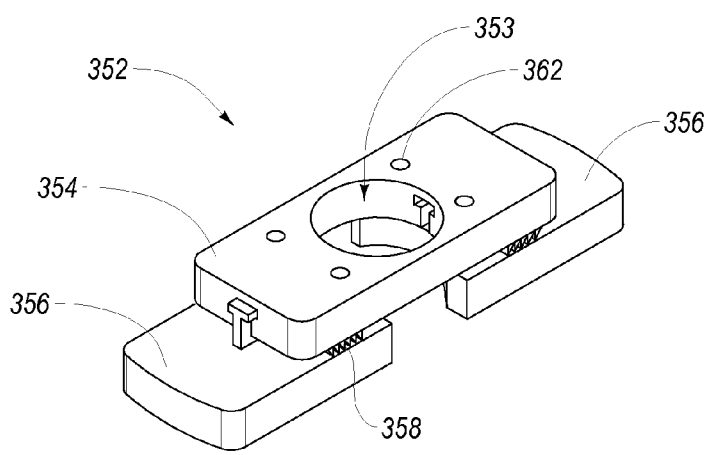
FIG. 3B illustrates a perspective view of the needle removal device removed from the suturing system shown in FIG. 3A.

FIG. 3B is a perspective view of the needle removal device 352 removed from the suturing system 30. As shown, the needle removal device 352 may include a generally rectangular first member 354. A pair of generally rectangular sliding members 356 may be slidably attached to a bottom portion of the first member 354. In other embodiments, the first member and/or the sliding members 356 may have a generally cylindrical shape, a generally oval shape, a generally trapezoidal shape, or any other shape suitable to be positioned between the interlock wings 316. The first member 354 may have a length greater than a length of one or more of the sliding members 356. The first member 354 and/or the sliding members 356 may be made from polymers, polymeric composites, titanium, stainless steel, metal alloys, combinations thereof, or any other suitable materials.

The first member 354 may include a central aperture 353 extending therethrough configured to allow a stem 338 (shown in FIG. 4B) of the handle assembly 314 to pass through the first member 354. The central aperture 353 may also be configured to receive the needle shaft 312 such that the needle shaft 312 may selectively be drawn through the aperture 356 of the needle removal device 352. Accordingly, the needle shaft 312 and the needle removal device 352 may be configured to move axially relative to one another. The needle removal device 352 may be positioned proximal the sheath hub 348. In other embodiments, the needle removal device 352 may be positioned substantially within the sheath hub 348 and the sheath hub 348 may include cutouts or other features configured to allow access to the sliding members 356. Such a configuration may reduce the interference height of the needle removal device 352 within the handle assembly 314.

The first member 354 and the sliding members 356 may include a plurality of needle receptacles 362 extending therethrough. One or more of the needle receptacles 362 may have a circular, oval, teardrop-like, triangular, or other suitable cross-sectional geometric shape. The needle receptacles 362 may have a constant diameter or a varying diameter. The needle receptacles 362 may be configured and positioned in the first member 354 to generally correspond to needle lumens 336 (shown in FIG. 3A) exiting the proximal end of the guide body 302. Each sliding member 356 may include a pair of the needle receptacles 362 positioned and configured to selectively correspond to the needle lumens 336 and/or the needle receptacles 362 of the first member 354. Such a configuration may allow the needles 308 to be selectively received within the needle receptacles 362 of the first member 354 and the needle receptacles 362 of the sliding members 356 as the needles 308 exit the guide body 302 through the needle lumens 336. As shown, four needle receptacles 362 may be formed in the first member 354 about the central aperture 353 and two needle receptacles 362 may be formed in each sliding member 356. In other embodiments, four, six, eight, or any other suitable number of needle receptacles 362 may be formed in the first member 354 in any suitable configuration. Similarly, three, four, of any other suitable number of needle receptacles 362 may be formed in the sliding members 356. Moreover, the needle receptacles 362 are illustrated as being substantially identical, the needle receptacles 362 may have varying sizes and/or configurations. For example, the needle receptacles 362 in the first member 354 may be generally circular and the needle receptacles 362 of the sliding members 356 may be generally triangular.

Figure 3C:
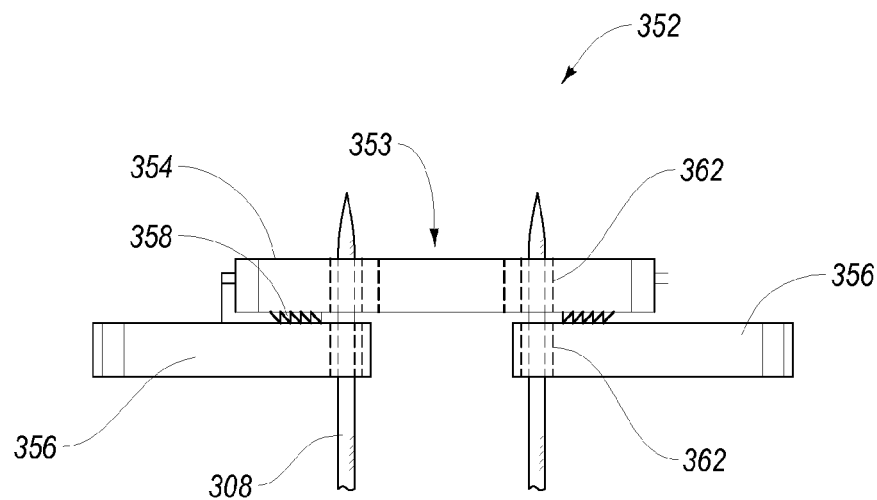
FIGS. 3C and 3D illustrate side views of the needle removal device shown in FIG. 3B in various configurations.
Figure 3D:
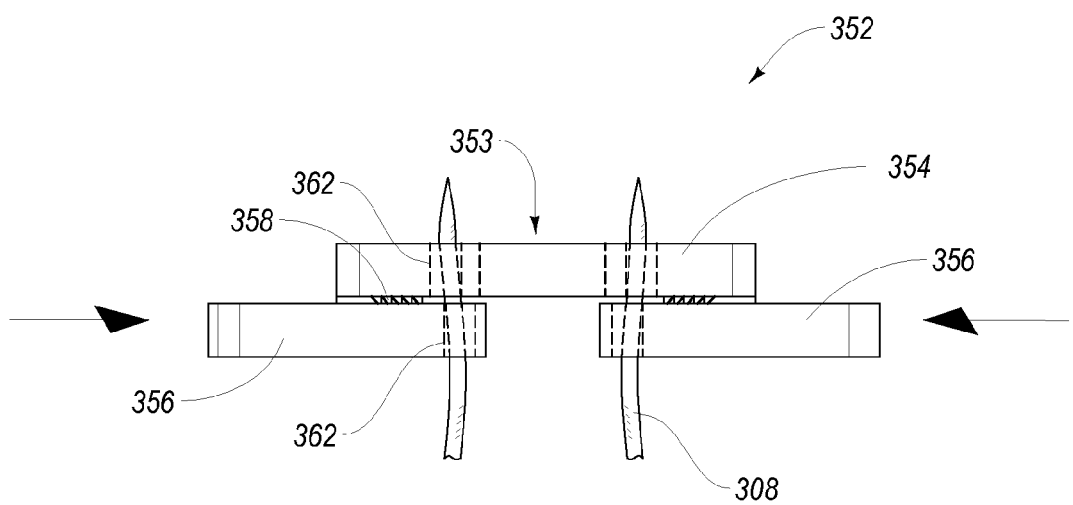

The needle removal device 352 may be configured to substantially secure the needles 308 within the needle removal device 352. For example, the needle removal device 352 may be moveable between a receiving position, wherein the needle receptacles 362 of the first member 354 and the sliding members 356 are substantially aligned as shown in FIG. 3C, and a deforming position, wherein the needle receptacles 362 of the first member 354 and the needle receptacles 362 of at least one of the sliding members 356 are substantially unaligned as shown in FIG. 3D. In the deforming position, the first member 354 and/or at least one sliding member 356 may at least partially deform a portion of two or more of the needles 308 extending through the needle receptacles 362 to pinch and/or lock the needles 308 between the first member 354 and at least one of the sliding members 356. Such a configuration may allow a user to secure the needles 308 within the needle removal device 352. In the deforming position, the needle removal device 352 may also be configured to allow a user to exert a force in the proximal direction on the needles 308 to overcome an initial resistance to removal of the needles 308 from the guide body 302. For example, the needle removal device 352 may be configured to allow a user to exert a force of about one quarter (0.25) pound-force to seventy (70) pound-force; about one (1) pound-force to sixty (60) pound-force; or about five (5) pound-force to forty (40) pound-force on the needles 308. In other embodiments, the needle removal device 352 may be configured to allow a user to exert larger or smaller forces on the needles 308.

Similar to the needle removal device 152, the needle removal device 352 may include one or more locking features configured to selectively lock the needle removal device 352 in the deforming position. For example, the first member 354 may include a plurality of teeth formed in the bottom surface thereof. The sliding members 356 may include a plurality of teeth formed in a top surface thereof. The teeth of the sliding members 356 may be configured to selectively interlock with the teeth of the first member 354 when the needle removal device 352 is moved toward the deforming position. Such a configuration may allow a user to lock the needle removal device 352 in the deforming position before removing the needles 308 from the guide body 302. In another embodiment, each sliding member 356 may include one or more grooves configured to selectively receive and lock onto one or more bar-like members extending across the bottom surface of the first member 354 when the needle removal device 352 is moved toward the deforming position. In other embodiments, the first member 354 and the sliding members 356 may include a catch system, a key and receiver type system, or any other suitable locking feature. In other embodiments, the locking features may be omitted.

Figures 4A, 4B, 4C:
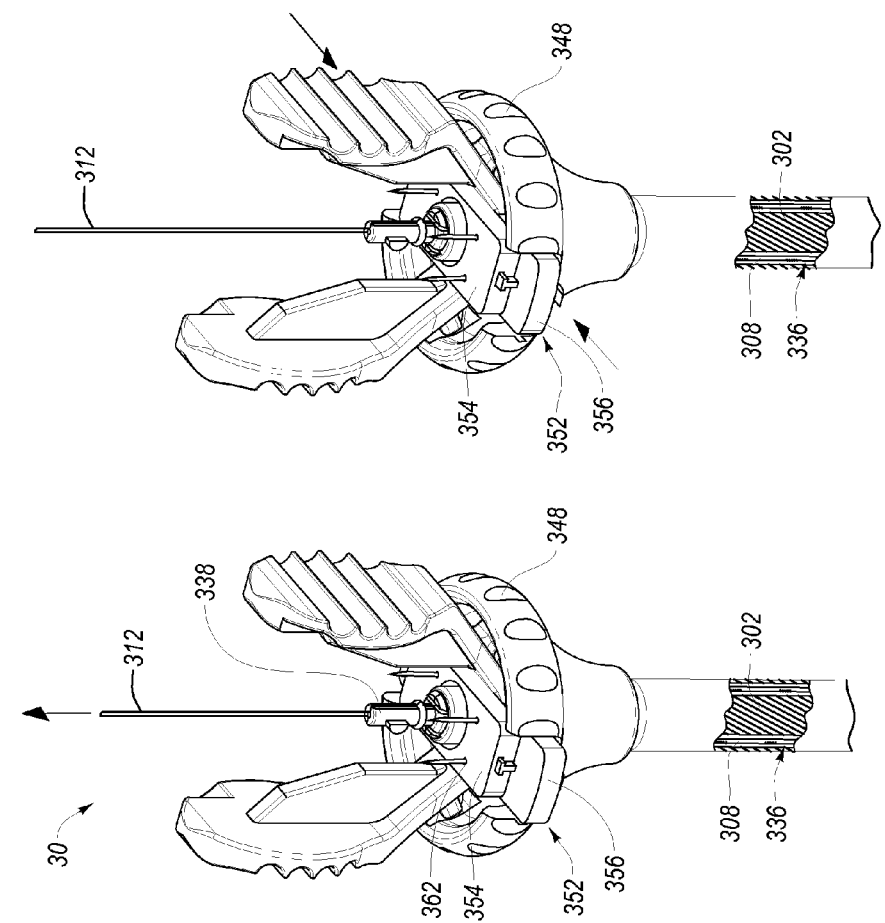
FIGS. 4A-4C illustrate steps for removing needles from the suturing system shown in FIG. 3A.

FIGS. 4A through 4C illustrate steps for removing the needles 308 from the suturing device 30 with the needle removal device 352. While the method is illustrated using the suturing system 30 and the needle removal device 352, it will be appreciated that the described method may utilize any other needle removal device and/or suturing system disclosed herein. Only certain exemplary steps of removing the needles 308 from the suturing system 30 are shown and described, however, it will be appreciated that the method may follow delivery of needles and suture lengths through body tissue or a vessel wall by the suturing system 30. For example, the method may include any of the steps previously described and/or illustrated in relation to FIGS. 2A through 2E.

Referring now to FIG. 4A, to deploy the needles 308, the handle 318 (shown in FIG. 3A) may be drawn proximally relative to the guide body 302 to proximally move the needle shaft 312. As shown, the needle shaft 312 may draw the needles 308 proximally through the needle lumens 336 of the guide body 302 until the needles 308 exit the guide body 302 within the hub 348. As the needles 308 exit the guide body 302, the needles 308 may be received within the needle receptacles 362 of the first member 354 and the needle receptacles 362 of one or more of the sliding members 356 while the needle removal device 352 is in the receiving position as shown.

Referring now to FIG. 4B, the sliding members 356 may be squeezed or pushed together relative to the first member 354 such that the needle removal device 352 moves toward the deforming position. As the first member 354 and/or the sliding members 356 slide relative to one another and toward the deforming position, the first member 354 and/or the sliding members 356 may at least partially deform the needles 308 extending through the needle receptacles 362 by, for example, subjecting the needles 308 to shear forces. The deformed portion of the needles 308 may then cause the needles 308 to become pinched or locked between the first member 354 and/or the sliding members 356. In the deforming position, one or more of the teeth of the first member 354 may interlock with one or more of the teeth of the one or more sliding members 356 to lock the needle removal device 352 in the deforming position.

Referring now to FIG. 4C, with the needle removal device 352 locked in the deforming position, the needle removal device 352 may be moved proximally relative to the guide body 302. Proximal movement of the needle removal device 352, in turn, may continue to remove the needles 308 from the guide body 302. Once the needles 308 are removed from the guide body 302, suture lengths (not shown) attached to the needles 308 may be cut and the needles 308 may be disposed of.

Another embodiment of a needle removal device will now be described in relation to FIGS. 5A through 6C. A suturing system 50 may be similar in many respects to the suturing systems 10 and 30 previously described in FIGS. 1A-4C. To the extent features or components of this configuration function in a manner similar to that as described above, such disclosure is hereby incorporated into the following additional configuration. Like structures and/or components are given like reference numerals. For ease of reference, only the proximal portion of the suturing system 50 is shown and described. The distal components may be manipulated by the proximal components in a similar manner as described with reference to FIGS. 1A through 2E.

Figure 5A:
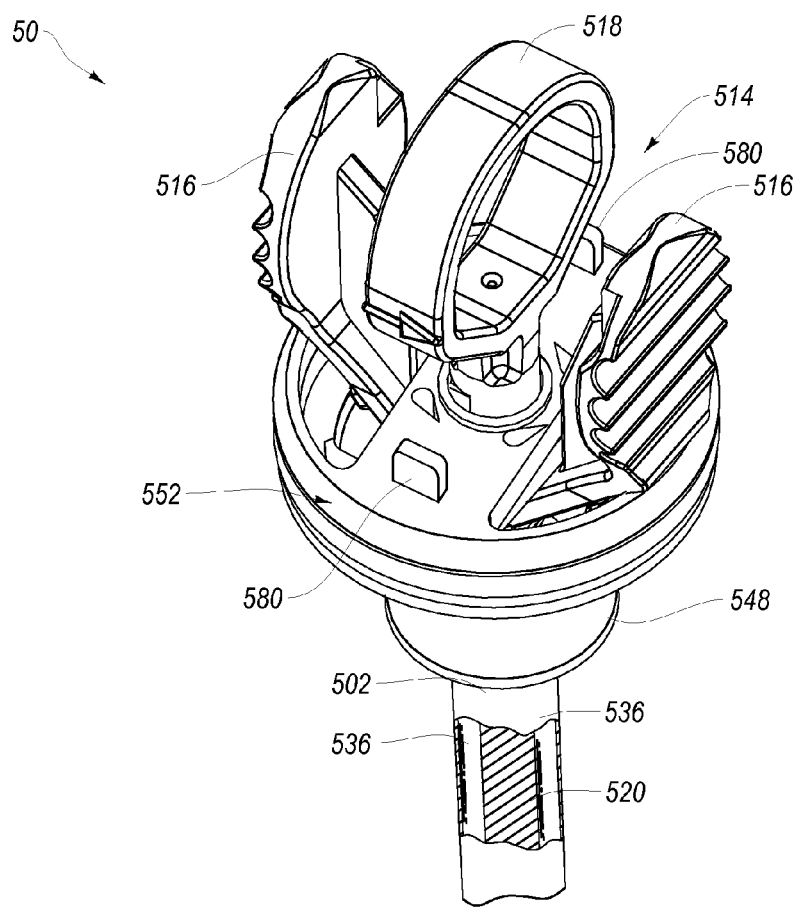
FIG. 5A illustrates a partial perspective view of a suturing system according to another embodiment.

FIG. 5A is a partial perspective view of the suturing system 50. The suturing system 50 may include a guide body 502, a needle guide (not shown) secured to a distal end of the guide body 502, and a flexible tube (not shown) secured to a distal end of the needle guide. A sheath 520 may be rotatably received over the guide body 502. A plurality of needles 508 (shown in FIG. 6A) may be mounted with their distal ends in a support holster (not shown) and attached to a movable needle shaft 512 (shown in FIG. 6A). A handle assembly 514 may be attached to a proximal end of the guide body 502. The handle assembly 514 may include a pair of interlock wings 516, a needle removal device 552, and a handle 518. The handle 518 may be attached to a proximal end of the needle shaft 512 and may be pulled proximally in order to draw the needles 508 from the flexible tube, through the needle guide and into the guide body 502 until the tips of the needles 508 emerge from the guide body 502 within a hub 548 of the sheath 520. Once the needles 508 emerge within the hub 548, the needles 508 may be received in the needle removal device 552. The hub 548 and the interlock wings 516 may be configured such that the needle removal device 552 may be positioned substantially adjacent exit points of the needles 508 from the guide body 502. For example, the hub 548 and the interlock wings 516 may have widths configured to allow the needle removal device 552 to rest at least partially on the hub 548 and to allow the needle removal device 552 to pull past the interlock wings 516. In another embodiment, the widths of the hub 548 and the distal portion of the interlock wings 516 may be configured to allow the needle removal device 552 to be positionable between the interlock wings 516 and a stem 538.

Figure 5B:
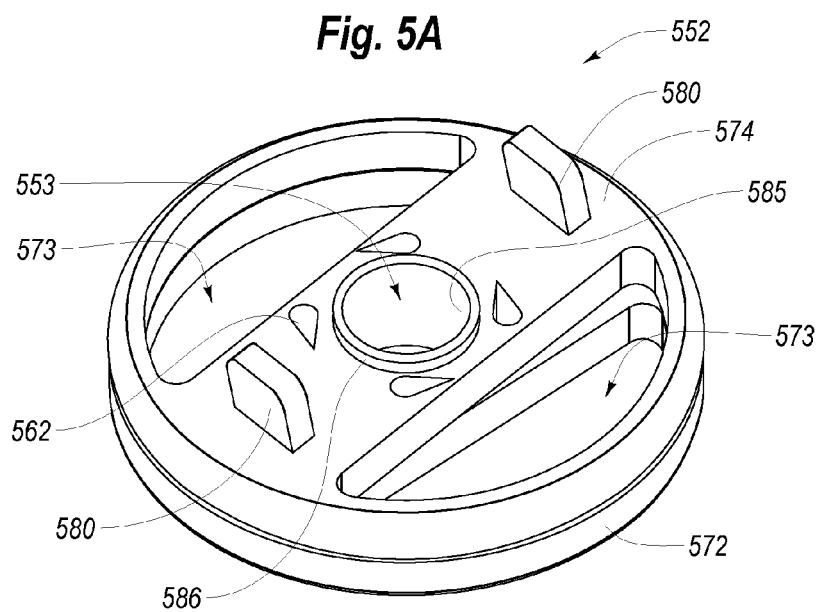
FIG. 5B illustrates a perspective view of the needle removal device removed from the suturing system shown in FIG. 5A.

FIG. 5B is a perspective view of the needle removal device 552 removed from the suturing system 50. The needle removal device 552 may include a first ring 572, a second ring 574 and a central aperture 553 extending therethrough. Both the first ring 572 and the second ring 574 may have a generally cylindrical geometric shape with substantially the same diameters. In other embodiments, the first ring 572 and/or the second ring 574 may have a generally cruciate geometric shape, a generally rectangular geometric shape, a generally oval geometric shape, or any other suitable shape and/or configuration. The first ring 572 and/or the second ring 574 may be made from polymers, polymeric composites, titanium, stainless steel, metal alloys, combinations thereof, or any other suitable material.

The needle removal device 552 may include one more features configured to allow the interlock wings 516 to selectively pass through the needle removal device 552. For example, the first ring 572 and/or the second ring 574 may each include a pair of wing cutouts 573. Each wing cutout 573 may have a semi-circular-like shape sized and configured to selectively allow the needle removal device 552 to pass over the interlock wings 516 such that the needle removal device 552 may be removed from the suturing system 50. In other embodiments, the wing cutouts 573 may have a generally rectangular, a generally oval, a generally triangular shape, or any other shape suitable to allow the needle removal device 552 to pass over the interlock wings 516. In yet other embodiments, the wing cutouts 573 may be omitted from the needle removal device 552. For example, the needle removal device 552 may be sized and configured to fit between the interlock wings 516 such that the interlock wings 516 extend about the needle removal device 552 rather than through the needle removal device 552.

The central aperture 553 may extend through the first ring 572 and the second ring 574 and may be configured to allow a stem 538 (shown in FIG. 6A) of the handle assembly 514 to pass through the needle removal device 552 such that the needle removal device 552 may be selectively positioned between the guide body 502 and the handle 518. The central aperture 553 may also be configured to receive the needle deployment shaft 512 such that the needle deployment shaft 512 may be selectively drawn through the needle removal device 552. Such a configuration allows the needle deployment shaft 512 and the needle removal device 552 to move axially relative to one another.

The needle removal device 552 may also include one or more features configured to selectively receive the needles 508 within the needle removal device 552. For example, the first ring 572 and the second ring 574 may each include a plurality of needle receptacles 562 extending therethrough. The needle receptacles 562 may be positioned circumferentially about the central aperture 553 and may be configured to selectively correspond to the needle lumens 536 exiting the proximal end of the guide body 502. One or more of the needle receptacles 562 may have a generally teardrop-like shape including a head portion and a tail portion. As discussed in more detail below, the tail portion of the needle receptacles 562 of the first ring 572 may be generally opposite the tail portion of the needle receptacles 562 of the second ring 574. The teardrop-like shaped needle receptacles 562 may provide a larger target for the needles 508 to pass through. In other embodiments, the one or more of the needle receptacles 562 may have a generally triangular shape, a generally oval shape, a generally conical shape, a generally cylindrical shape, a generally circular shape, combinations thereof, or any other suitable shape. While four needle receptacles 562 are shown surrounding the first central aperture 553 in the first ring 572 and the second ring 574, three, five, six, or any other suitable number of needle receptacles 562 may be possible in any suitable configuration. Moreover, while the first ring 572 and the second ring 574 are shown having similar needle receptacles 562, in other embodiments, the first ring 572 and the second ring 574 may include needle receptacles having different sizes, shapes, and/or configurations. For example, the first ring 572 may include oval shaped needle receptacles 562 and the second ring 574 may include teardrop-like shape needle receptacles 562 or the first ring 572 may include generally rectangular shaped needle receptacles 562 and generally triangular shaped needle receptacles 562.

The first ring 572 and the second ring 574 of the needle removal device 552 may be rotatably attached. For example, the first ring 572 may include a hollow shaft 585 attached to an upper surface of the first ring 572. The central aperture 553 extending through the second ring 574 may be configured to receive the hollow shaft 585 of the first ring 572 such that the second ring 574 may rotate about the hollow shaft 585. The hollow shaft 585 may include a flanged end portion 586 configured to maintain the second ring 574 on the hollow shaft 585. The hollow shaft 585 may also be sized and configured such that the needle deployment shaft 512 may pass through the hollow shaft 585. In other embodiments, the hollow shaft 585 may be attached to the second ring 574 rather than the first ring 572 and may be configured to allow the first ring 572 to rotate about the hollow shaft 585. In yet other embodiments, the first ring 572 and/or the second ring 574 may include a track system configured to allow the first ring 572 and/or the second ring 574 to rotate relative to one another.

Figure 5C:
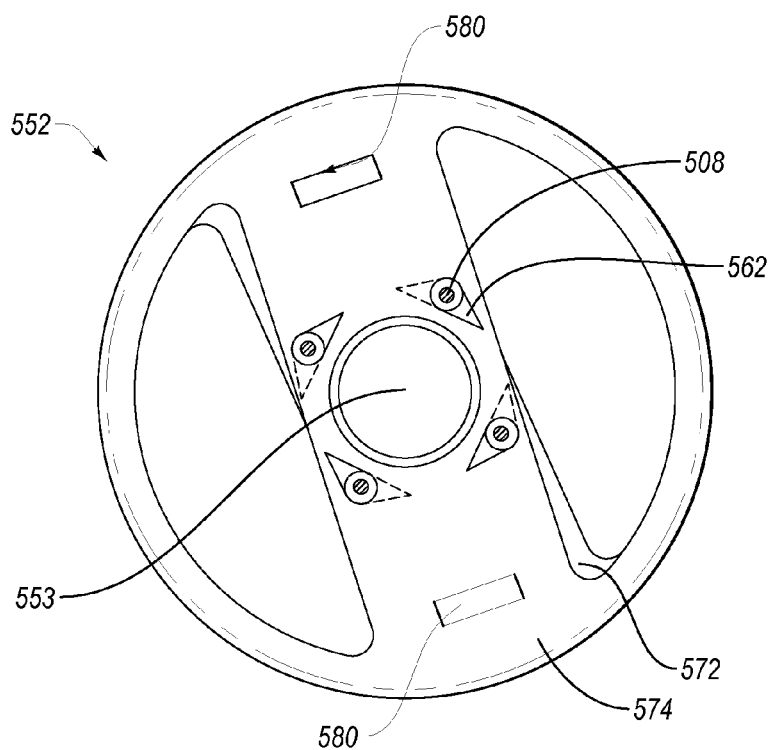
FIGS. 5C and 5D illustrate top plan views of the needle removal device shown in FIG. 5B in various configurations.
Figure 5D:
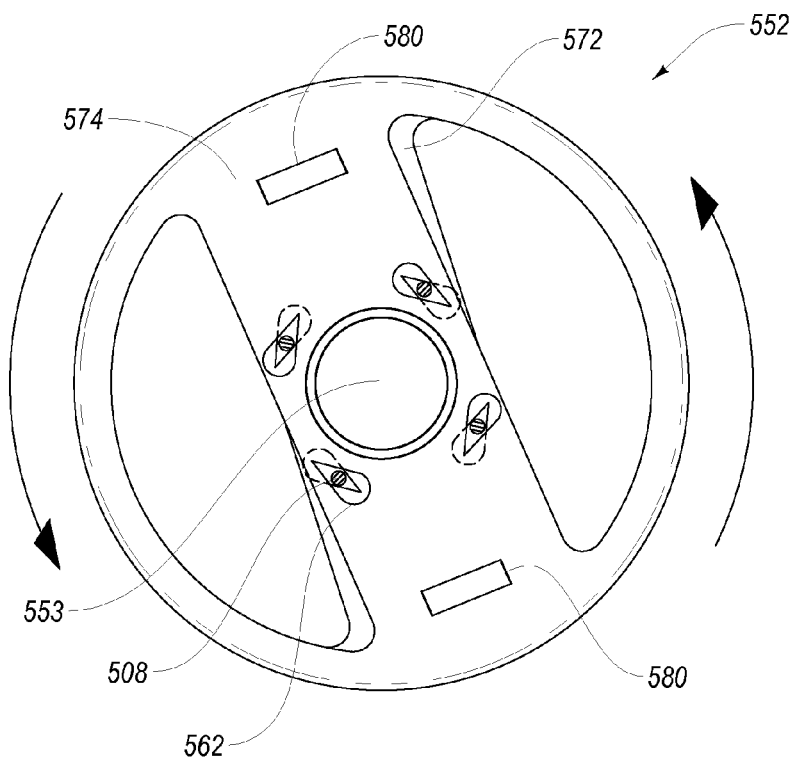

The needle removal device 552 may also include features configured to substantially lock or pinch the needles 508 within the needle removal device 552. FIG. 5C is a top view of the needle removal device 552. Relative rotation between the first ring 572 and the second ring 574 may cause the needle removal device 552 to move between a receiving position and a deforming position. In the receiving position as shown in FIG. 5C, the needle receptacles 562 of the first ring 572 and the needle receptacles 562 of the second ring 574 may be substantially aligned such that needles 508 (shown in FIG. 6A) may freely pass through the needle receptacles 562. In the deforming position as shown in FIG. 5D, relative rotation between the first ring 572 and the second ring 574 may cause the needle receptacles 562 of the first ring 572 and the needle receptacles 562 of the second ring 574 to become substantially unaligned. As the needle removal device 552 moves toward the deforming position, the first ring 572 and/or the second ring 574 may exert shear forces or twisting forces on the portion of the needles 508 extending through the needle receptacles 562 such that the needles 508 at least partially deform to pinch or lock the needles 508 between the first ring 572 and the second ring 574. As discussed above, the tail portion of the needle receptacles 562 in the first ring 572 and the tail portion of the needle receptacles 562 in the second ring 574 may be generally opposite such that the needles 508 may become wedged or lodged between the converging tail portions. Such a configuration may enhance the grasp of the needle removal device 552 on the needles 508. In yet other embodiments, the needle receptacles 562 may include one or more grasping features such as ridges, textured surfaces, contoured surfaces, adhesive, magnets, or other features suitable to enhance the grasp of the needle removal device 552 on the needles 508. For example, the needle receptacles 562 may include sharpened edges configured to at least partially cut into an outer surface of the needles 508 in order to enhance the grasp of the needle removal device 552 on the needles 508.

Like the needle removal devices 152 and 352, the needle removal device 552 may include locking features configured to selectively lock the needle removal device in the deforming position. For example, the needle removal device 552 may include one or more detents configured to selectively lock the needle removal device 552 in the deforming position. In another embodiment, both the first ring 572 and the second ring 574 may include one or more holes and one or more locking pins. For example, when the needle removal device 552 is moved into the deforming position, the one or more holes may be substantially aligned such that the one or more of the locking pins may be inserted in the one or more holes through both the first ring 572 and the second ring 574 to lock the needle removal device 552 in the deforming position.

The needle removal device 552 may also be configured to help a user to remove the needles 508 from the suturing system 50. For example, the needle removal device 552 may be configured to allow a user to exert a force in the proximal direction on the needles 508 to overcome an initial resistance to removal of the needles 508 from the guide body 502. The needle removal device 552 may be configured to allow a user to exert a force in the proximal direction of about one quarter (0.25) pound-force to seventy (70) pound-force; about one (1) pound-force to sixty (60) pound-force; or about five (5) pound-force to forty (40) pound-force on the needles 508. In other embodiments, the needle removal device 552 may be configured to allow a user to exert larger or smaller forces on the needles 508.

The needle removal device 552 may also include features configured to help a surgeon or user to manipulate the needle removal device 552. For example, the second ring 574 may include one or more gripping portions 580 configured to help a user move the needle removal device 552 between the receiving and deforming positions. In addition, the one or more gripping portions 580 may be configured to help a user move the needle removal device 552 proximally away from the hub 548. The one or more gripping portions 580 may be configured as one or more tabs as shown in FIG. 5B. Each of the one or more tabs may have a length of about 1 cm to 7 cm; about 2 cm to 6 cm; or about 3 cm to 5 cm. In other embodiments, the lengths of the one or more tabs may be greater or smaller. In yet other embodiments, the gripping portion 580 may be configured as a textured surface or as ridges formed on a lateral surface of the second ring 574. In other embodiments, the gripping portion 580 may be formed on the first ring 572 rather than on the second ring 574 or on both the first ring 572 and the second ring 574.

FIGS. 6A through 6C illustrate steps for removing the needles 508 from the suturing device 50 with the needle removal device 552. While the method is illustrated using the suturing system 50 and the needle removal device 552, it will be appreciated that the described method may utilize any other needle removal device and/or suturing system disclosed herein. Only certain exemplary steps of removing the needles 508 from the suturing system 50 are shown and described, however, it will be appreciated that the method may follow delivery of needles and suture lengths through body tissue or a vessel wall by the suturing system 50. For example, the method may include any of the steps previously described and/or illustrated in relation to FIGS. 2A through 2E.

Referring now to FIG. 6A, to deploy the needles 508, the handle 518 (shown in FIG. 5A) may be drawn proximally relative to the guide body 502 to proximally move the needle shaft 512. As shown, the needle shaft 512 may draw the needles 508 proximally through the needle lumens 536 of the guide body 502 until the needles 508 exit the guide body 502 within the hub 548. As the needles 508 exit the guide body 502, the needles 508 may be received within the needle receptacles 562 of the first ring 572 and the needle receptacles 562 of the second ring 574 while the needle removal device 552 is in the receiving position as shown.

Referring now to FIG. 5B, the first ring 572 and/or the second ring 574 may be rotated relative to the other ring such that the needle removal device 552 moves toward the deforming position. As the first ring 572 and/or the second ring 574 rotates relative to one another, the first ring 572 and/or the second ring 574 may at least partially deform the needles 508 extending through the needle receptacles 562. The deformed portion of the needles 508 may then cause the needles 508 to become pinched or locked between the first ring 572 and/or the second ring 574.

Figure 7A:
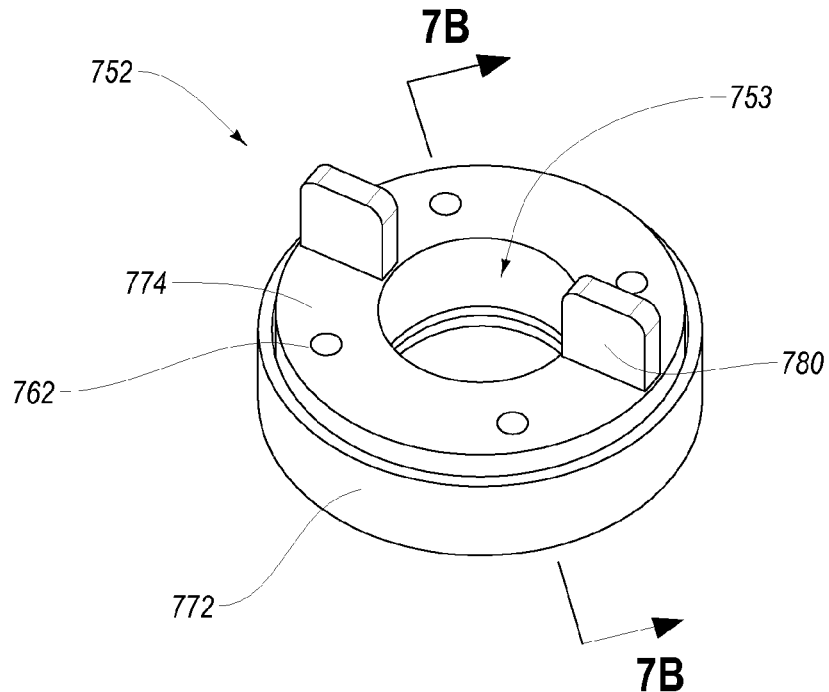
FIG. 7A illustrates a perspective view of a needle removal device according to another embodiment.
Figure 7B:
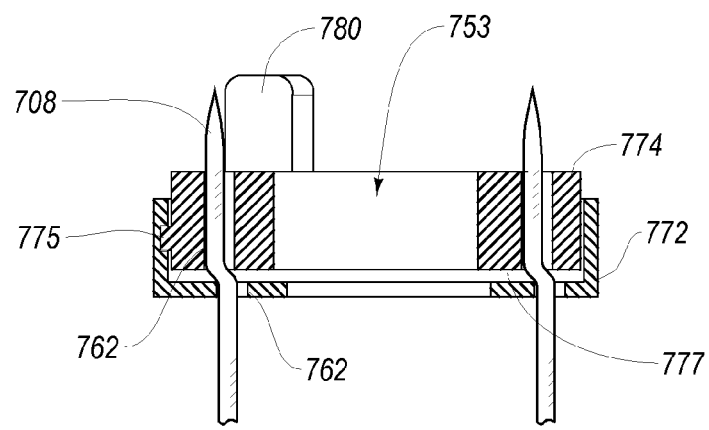
FIG. 7B illustrates a cross-sectional view of the needle removal device shown in FIG. 7A taken along section line 7B-7B.

Referring now to FIG. 5C, with the needle removal device in the deforming position, the needle removal device 552 may be moved proximally relative to the guide body 502. Proximal movement of the needle removal device 552, in turn, may continue to remove the needles 508 from the guide body 502. Once the needles 508 are removed from the guide body 502, suture lengths (not shown) attached to the needles 508 may be cut and the needles 508 may be disposed of FIGS. 7A and 7B illustrate another embodiment of a needle removal device 752. As shown, the needle removal device 752 may be similar in many respects to the needle removal device 552. For example, the needle removal device 752 may include a first ring 772, a second ring 774, one or more tabs 780, and a central aperture 753 extending through the first ring 772 and the second ring 774. In other embodiments, the one or more tabs 780 may be omitted. The needle removal device 752 may be sized and configured to fit between interlock wings of a suturing system such that the interlock wings extend about the needle removal device 752. In other embodiments, the needle removal device 752 may include wing cutouts configured to allow interlock wings to selectively pass through the needle removal device 752.

The first ring 772 and the second ring 774 of the needle removal device 752 may be rotatable relative to one another. In some embodiments, only one of the first ring 772 and/or the second ring 774 may be rotatable relative to the other ring. For example, the first ring 772 may include one or more receptacles configured to selectively receive one or more pins extending from a hub of a suturing system. When the needle removal device 752 is positioned on the suturing system, the one or more pins may restrict rotation of the first ring 772 while the second ring 774 may be rotatable about a stem of the suturing system. Similar to the needle removal device 552, the first ring 772 and the second ring 774 may each include a plurality of needle receptacles 762 extending therethrough and may be moveable between a receiving position and a deforming position. In the receiving position, the needle receptacles 762 of the first ring 772 and the needle receptacles 762 of the second ring 774 may be substantially aligned such that needles (shown in FIG. 7B) may freely pass through the needle receptacles 762. In the deforming position, the needle receptacles 762 of the first ring 772 and the needle receptacles 762 of the second ring 774 may become substantially unaligned such that the needles 708 at least partially deform to pinch or lock the needles between the first ring 772 and the second ring 774 as shown in FIG. 7B. One or more of the needle receptacles 762 may have a generally circular shape, a generally square shape, a generally triangular shape, a generally teardrop like shape, combinations thereof, or any other suitable shape.

As shown in FIG. 7B, the first ring 772 may include a recess 777 configured to receive the second ring 774 such that at least a portion of the second ring 774 may be positioned within or nested in the recess 777 of the first ring 772. In other embodiments, more or less of the second ring 774 may be positioned within the recess 777 of the first ring 772. For example, the second ring 774 may be completely positioned within the recess 777 of the first ring 772. Such a configuration may reduce the interference height of the needle removal device 752, for example within a handle assembly of the suturing system. Moreover, the needle removal device 752 may include one or more locking features configured to lock the first ring 772 and/or the second ring 774 in the deforming position. For example, the needle removal device 752 may include one or more detents 775 configured to lock the second ring 774 in place once the second ring 774 rotates into the deforming position. In other embodiments, the one or more locking features may be omitted.

FIGS. 8A and 8B illustrate another embodiment of a needle removal device 852. As shown, the needle removal device 852 may be similar in many respects to the needle removal device 552 and/or the needle removal device 752. For example, similar to the needle removal device 552 and/or the needle removal device 752, the needle removal device 852 may include a first ring 872, a second ring 874, one or more gripping features 880, and/or central aperture 853 extending through the first ring 872 and the second ring 874. Similar to the needle removal device 552, the first ring 872 and/or the second ring 874 may be rotatable and each may include a plurality of needle receptacles 862 extending therethrough and may be moveable between a receiving position and a deforming position. In the receiving position, the needle receptacles 862 of the first ring 872 and the needle receptacles 862 of the second ring 874 may be substantially aligned such that needles (not shown) may freely pass through the needle receptacles 862. In the deforming position, the needle receptacles 862 of the first ring 872 and the needle receptacles 862 of the second ring 874 may become substantially unaligned such that the needles at least partially deform to pinch or lock the needles between the first ring 872 and the second ring 874. One or more of the needle receptacles 862 may have a generally circular shape, a generally square shape, a generally triangular shape, a generally tadpole-like shape, combinations thereof, or any other suitable shape.

As shown, the first ring 872 of the needle removal device 852 may be sized and configured to at least partially overlap a hub 848 of a suturing system 80. For example, the first ring 872 may have a diameter greater than a diameter of the hub 848 and may include a collar portion 872A that extends about at least a portion of an outer surface 848A of the hub. The collar portion 872A may be configured such that the collar portion 872A may pass over the hub 848 when the needle removal device 852 is moved proximally from the hub 848. For example, the collar portion 872A may be made from one or more substantially flexible materials such that the collar portion 872A may flex to pass over the hub 848 when the needle removal device 852 is moved proximally from the hub 848. In another embodiment, the first ring 872 may be sized and configured to at least partially underlap the hub 848. Such a configuration may reduce the interference height of the needle removal device 852 within a handle assembly of the suturing system 80.

In yet other embodiments, needle removal devices may be configured to secure needles for removal from suturing systems by selectively receiving and grasping on the needles extending proximally from the suturing device as described in U.S. patent application, entitled "Needle Removal Devices, Systems and Methods," Ser. No. 13/610,598, filed on the same day, the disclosure of which is incorporated herein in its entirety.

Embodiments of the suturing device, needle removal device and the like may include a material made from any of a variety of known suitable biocompatible materials, such as a biocompatible shape memory material (SMM). For example, the SMM may be shaped in a manner that allows for the needle removal device to automatically move from the receiving position to the deforming position when needles are received within the needle receptacles. SMMs have a shape memory effect in which they may be made to remember a particular shape. Once a shape has been remembered, the SMM may be bent out of shape or deformed and then returned to its original shape by unloading from strain or heating. Typically, SMMs may be shape memory alloys (SMA) comprised of metal alloys, or shape memory plastics (SMP) comprised of polymers. The materials may also be referred to as being superelastic.

Usually, an SMA may have an initial shape that may then be configured into a memory shape by heating the SMA and conforming the SMA into the desired memory shape. After the SMA is cooled, the desired memory shape may be retained. This allows for the SMA to be bent, straightened, twisted, compacted, and placed into various contortions by the application of requisite forces; however, after the forces are released, the SMA may be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios or by the conditions of manufacture.

For example, the primary material of needle removal device may be of a NiTi alloy that forms superelastic nitinol. Also, additional materials may be added to the nitinol depending on the desired characteristic. The alloy may be utilized having linear elastic properties or non-linear elastic properties.

An SMP is a shape-shifting plastic that may be fashioned into the needle receptacles in accordance with the present disclosure. Also, it may be beneficial to include at least one layer of an SMA and at least one layer of an SMP to form a multilayered body; however, any appropriate combination of materials may be used to form a multilayered device. When an SMP encounters a temperature above the lowest melting point of the individual polymers, the blend makes a transition to a rubbery state. The elastic modulus may change more than two orders of magnitude across the transition temperature ($T_{tr}$). As such, an SMP may be formed into a desired shape of an endoprosthesis by heating it above the $T_{tr}$, fixing the SMP into the new shape, and cooling the material below $T_{tr}$. The SMP may then be arranged into a temporary shape by force and then resume the memory shape once the force has been released. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present disclosure.

The needle receptacles and the like may have at least one layer made of an SMM or suitable superelastic material and other suitable layers that can allow the needle receptacles to automatically grasp onto the needles.

Also, the needle removal devices, the needle receptacles or other aspects or components of the system may be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/0312740, which are each incorporated herein by reference, in their entireties) cobalt-chromium alloys, or other known biocompatible materials. Such biocompatible materials may include a suitable biocompatible polymer in addition to or in place of a suitable metal. The polymeric needle removal device may include biodegradable or bioabsorbable materials.

In one embodiment, the needle removal device and/or needle receptacles may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol knot replacement element. The nitinol needle removal device has improved radiopacity yet retains its superelastic and shape memory behavior and further maintains a thin body thickness for high flexibility.

In one embodiment, the needle removal device and/or the needle receptacles may be made at least in part of a high strength, low modulus metal alloy comprising Niobium, Tantalum, and at least one element selected from the group consisting of Zirconium, Tungsten, and Molybdenum.

In further embodiments, the needle removal device and/or the needle receptacles may be made from or be coated with a biocompatible polymer. Examples of such biocompatible polymeric materials may include hydrophilic polymer, hydrophobic polymer biodegradable polymers, bioabsorbable polymers, and monomers thereof. Examples of such polymers may include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

The coatings can also be provided on the system or components thereof to facilitate the loading or delivery of beneficial agents or drugs, such as therapeutic agents, pharmaceuticals and radiation therapies.

The invention is susceptible to various modifications and alternative means, and specific examples thereof have been shown by way of example in the drawings and are herein described in detail. It should be understood, however, that the invention is not to be limited to the particular systems or methods disclosed, but to the contrary; the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device comprising:
   a plurality of needles;
   one or more sutures, each of the one or more sutures having an end attached to one of the plurality of needles;
   a guide body having a proximal end, a distal end, an internal lumen configured to receive at least a portion of the one or more sutures, and a plurality of needle lumens configured to receive the plurality of needles;
   a shaft moveably positioned within the guide body, the shaft being operably connected to the plurality of needles such that proximal movement of the shaft draws the plurality of needles into the plurality of needle lumens; and
   a needle removal device removably attached to the proximal end of the guide body, the needle removal device comprising:
   a first member having a first plurality of needle receptacles extending therethrough, the first needle receptacles being configured and positioned to correspond to the plurality of needle lumens of the guide body; and
   a second member having a second plurality of needle receptacles extending therethrough, wherein at least one of the first member or the second member is moveable between a first position, wherein the first needle receptacles and the second needle receptacles are substantially aligned, and a second position, wherein the first needle receptacles and the second needle receptacles are substantially unaligned.

2. The device of claim 1, wherein the first position is configured to allow at least one of the plurality of needles to be moveable within at least one of the first needle receptacles or the second needle receptacles, and wherein the second position is configured to at least partially deform the at least one or more of the plurality of needles between the first member and the second member to substantially lock the one or more needles within at least one of the first needle receptacles or the second needle receptacles.

3. The device of claim 2, wherein the second position is further configured to allow a user to exert a force in a proximal direction of about one (1) to seventy (70) pound-force on at least one of the plurality of needles to remove the one or more needles from the suturing device.

4. The device of claim 1, further comprising one or more locking features configured to substantially lock at least one of the first member or the second member in the second position.

5. The device of claim 4, wherein the one or more locking features comprise a first plurality of teeth on the first member and a second plurality of teeth on the second member, wherein the second plurality of teeth are configured to selectively engage the first plurality of teeth in the second position.

6. The device of claim 4, wherein the one or more locking features comprise one or more detents.

7. The device of claim 1, wherein one or more of the first needle receptacles have a generally teardrop-like shape including a first head portion and a first tail portion, and wherein one or more of the second needle receptacles have a generally teardrop-like shape including second head portion and a second tail portion, and wherein the second head portion is generally opposite the first head portion.

8. The device of claim 7, wherein the first needle receptacles and the second needle receptacles are configured to wedge one or more needles between the first tail portions and the second tail portions.

9. The device of claim 1, wherein the first member comprises a first ring and the second member comprises a second ring, wherein at least the second ring is rotatable relative to the first ring.

10. The device of claim 9, wherein the first ring includes a recess configured to receive at least a portion of the second ring.

11. The device of claim 9, wherein the first ring includes a collar portion configured to at least partially overlap a hub of a suturing device.

12. The device of claim 9, wherein at least one of the first ring or the second ring includes one or more tabs having a length between about 1-cm to 7-cm.

13. The device of claim 9, further comprising one or more gripping portions on at least one of the first ring or the second ring, wherein the one or more gripping portions are configured to at least help a user move the at least one of the first ring or the second ring between the first position and the second position.

14. The device of claim 1, wherein the second member is slidably attached to the first member.

15. The device of claim 14, wherein at least one of the first member or the second member includes a central opening extending therethrough, wherein the central opening has a generally rounded rectangular geometric shape.

16. The device of claim 14, further comprising a third member slidably attached to the first member, the third member being generally opposite the second member and having a third plurality of needle receptacles extending therethrough.

17. A method of removing one or more needles from a suturing device having one or more needle lumens, the method comprising:
   inserting a suturing device into a patient, the suturing device comprising:
   a plurality of needles;
   one or more sutures, each of the one or more sutures having an end attached to one of the plurality of needles;
   a guide body having a proximal end, a distal end, an internal lumen configured to receive at least a portion of the one or more sutures, and a plurality of needle lumens configured to receive the plurality of needles;

a shaft moveably positioned within the guide body, the shaft being operably connected to the plurality of needles such that proximal movement of the shaft draws the plurality of needles into the plurality of needle lumens; and a needle removal device removably attached to the proximal end of the guide body, the needle removal device comprising:

a first member having a first plurality of needle receptacles extending therethrough, the first needle receptacles being configured and positioned to correspond to the plurality of needle lumens of the guide body; and a second member having a second plurality of needle receptacles extending therethrough, wherein at least one of the first member or the second member is moveable between a first position, wherein the first needle receptacles and the second needle receptacles are substantially aligned, and a second position, where in the first needle receptacles and the second needle receptacles are substantially unaligned;

positioning the needle removal device substantially adjacent the proximal end of the suturing device;

drawing one or more of the plurality of needles proximally through one or more of the one or more needle lumens of the suturing device until at least tips of the one or more needles exit from the proximal end of the suturing device;

receiving at least the tips of the one or more needles within one or more of the first plurality of needle receptacles and one or more of the second plurality of needle receptacles;

moving at least one of the first member or the second member to the second position to at least partially deform at least a portion of the one or more needles between the first member and the second member; and moving the needle removal device proximally relative to the suturing device to remove the one or more needles from the suturing device.

* * * * *